United States Patent [19]
Brandt

[11] Patent Number: 5,425,368
[45] Date of Patent: Jun. 20, 1995

[54] METHOD AND APPARATUS FOR ESTIMATING TISSUE VOLUMES IN MAGNETIC RESONANCE IMAGES

[75] Inventor: Michael E. Brandt, Houston, Tex.

[73] Assignee: Board of Regents, The University of Texas System, Austin, Tex.

[21] Appl. No.: 33,749

[22] Filed: Mar. 17, 1993

[51] Int. Cl.⁶ .............................................. A61B 5/055
[52] U.S. Cl. ........................... 128/653.2; 364/413.13; 382/128
[58] Field of Search ......................... 128/653.2, 653.1; 364/413.13, 413.14; 382/6

[56] References Cited

U.S. PATENT DOCUMENTS

| | | | |
|---|---|---|---|
| 4,712,560 | 12/1987 | Schaefer et al. | 128/653.2 |
| 4,729,098 | 3/1988 | Cline et al. | 128/653.1 |
| 4,856,528 | 8/1989 | Yang et al. | 382/6 |
| 4,961,425 | 10/1990 | Kennedy et al. | 128/653.1 |
| 5,113,357 | 5/1992 | Johnson et al. | 364/413.13 |
| 5,187,658 | 2/1993 | Cline et al. | 364/413.13 |
| 5,273,040 | 12/1993 | Apicella et al. | 364/413.13 |

OTHER PUBLICATIONS

Bensaid et al., "MRI Segmentation Using Supervised and Unsupervised Methods," *Annual International Conference of the IEEE Engineering in Medicine and Biology Society*, 13(1):60–61, 1991.
Romaniuk, S. G. and Hall, L. O., "Learning Fuzzy Information in a Hybrid Connectionist, Symbolic Model" *Proceedings of the Third International Workshop on Neural Networks and Fuzzy Logic, NASA Conference Publication 10111*, 1:13–29, 1992.

Primary Examiner—Lee S. Cohen
Assistant Examiner—Brian L. Casler
Attorney, Agent, or Firm—Arnold, White & Durkee

[57] ABSTRACT

A fuzzy logic approach to the problem of distinguishing cerebrospinal fluid, gray and white matter pixels in magnetic resonance images of the brain. An unsupervised fuzzy clustering procedure based on a variant of the fuzzy c-means algorithm computes automatically, with virtually no operator intervention, the percentage area of each of these three compartments in each image. Each volume element represented in the image can belong to all compartments in varying degrees. The procedure requires input of the number of different compartments in the image, as well as a parameter which determines the amount of overlap of compartment boundaries. Preliminary data processing involves noise removal from images by highpass filtering. The final solution is substantially independent of required initial estimates of the gray scale values that are most representative of the white, gray and cerebrospinal fluid compartments in the image. The method is useful in the diagnosis of hydrocephalus.

39 Claims, 8 Drawing Sheets

METHOD AND APPARATUS FOR ESTIMATING TISSUE VOLUMES IN MAGNETIC RESONANCE IMAGES

The government has certain rights in the invention. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The invention relates to methods and apparatus for estimating relative volumes of tissue types distinguishable in magnetic resonance (MR) images of the tissues.

2. Distinguishing Tissue Types in Brain Images

In vivo estimates of white matter, gray matter and cerebrospinal fluid (CSF) volumes are useful in diagnosis and treatment of several conditions affecting the brain, including Alzheimer's disease, Down's syndrome, senile dementia, and hydrocephalus. In the latter condition, communicating and non-communicating hydrocephalus can be distinguished by estimating CSF volume in images which include the brain ventricles. In other cases, the need for surgical intervention in hydrocephalic patients to establish or repair a CSF drainage shunt can be assessed with serial estimates of CSF contained within the brain ventricles. Diagnosis may also be aided because it has been observed that the ratio of white matter to gray matter in hydrocephalic children is much lower than in control (normal) children.

Computerized tomography (CT) scans and radionuclide ventriculography have been used to estimate ventricular volumes in the brain, but estimate of the error associated with single measurements using either of these techniques are in the range 20–30%. Additionally, reliable in vivo estimates of extraventricular cranial CSF volumes can not be obtained with CT or radionuclide techniques. Reasons for this include the inherently poor resolution of radionuclide techniques and, in the case of CT, the relatively poor contrast of CSF with other brain tissue in CT images.

Superior brain images, on the other hand, are obtained with MR because gray and white matter and CSF are usually visually differentiable in MR images. MR imaging is the first technique to allow in vivo investigations of gross brain structural variation with sufficient resolution to be clinically useful. MR images, however, require careful interpretation due to possible ambiguities in interpretation of the gray scale value of a particular image point or element (pixel).

Ambiguities may arise because a single gray scale pixel value from an MR image of the brain can represent mixed tissue types (e.g., gray matter and CSF). This occurs because of partial volume averaging, in which a given pixel value represents a volume element (voxel) containing more than one tissue type. For example, a given pixel in the image could be classified as 0.5 (50%) gray and 0.5 (50%) white, or 0.4 fluid and 0.6 gray.

The most common techniques to solve this volume averaging problem use some variation of a classification procedure which tries to estimate or find a boundary in the image to allow separation of tissue compartments. Another (rule-based) approach to classifying tissue types requires the choice of two empirical thresholds which may change from subject to subject. Pixel classification in this latter system, therefore, requires a specific model of the data which a particular patient may not fit optimally. Attempts to overcome these problems through use of statistical models and statistical pattern recognition approaches may succeed in avoiding reliance on specific models for the data, but their validity rests on assumptions regarding data distribution which cannot be confirmed in the case of particular patients. Additionally such schemes generally require clinical or operator judgment and this cannot be readily automated.

SUMMARY OF THE INVENTION

The present invention substantially avoids requirements for patient-specific assumptions and operator judgment in interpreting MR brain images. It allows accurate volumetric estimation of white matter, gray matter and CSF in suitable MR images through use of fuzzy logic techniques to classify image elements (pixels) by their gray scale values. In contrast to prior methods for MR image interpretation, the presently claimed fuzzy classification process for MR image pixels is fully automatic and executes very quickly on a modern personal computer or work station. The classification scheme does not require determination of a boundary in the image to separate tissue compartments, but instead recognizes that individual image pixels may represent two or more distinct tissue types at the same time.

Fuzzy Classification

The principle behind fuzzy classification is very simple. A good example of the need for such a system would be the concept of "age" as applied to a particular person. When is someone to be considered "young" or "old?" A classification scheme having a cutoff age above which a person would be considered (classified) as "old" would clearly have limited usefulness if applied uniformly to individuals. It is apparent that there is a continuum of ages through which a person passes in changing from "young" to "old." At age 80, a person is clearly old, and at age 20 clearly young, but at an intermediate age (perhaps 50), a person might be considered as being "partly old" and "partly young." Fuzzy logic, as applied in the present invention, recognizes the condition wherein a pixel in an MR image may represent elements from more than one group (e.g., white matter and gray matter). By considering the (possibly mixed) classification(s) of each pixel, methods of the present invention can produce accurate estimates of the total amount of tissue of each type comprising the image. In such applications, the present invention has several advantages over prior methods.

First, methods of the present invention are relatively fast, requiring about two minutes or less to analyze a single brain MR image to yield a decision on the percent of gray matter, white matter and CSF represented in the image. Second, the methods are substantially automatic, requiring no choice of tissue boundaries in the image and little human operator intervention. Third, the methods solve the volume averaging problem by allowing for mixed tissue representation in a single voxel. Fourth, the methods do not assume any a priori statistical or heuristic model of the data; a model for each image analyzed is estimated from the gray scale values for pixels in that image. Fifth, use of two or more different spectral channels of the same MR image (i.e., T1 and T2 weighted images and proton density images) provides additional information over that available from a single channel image, allowing more accurate discrimination of tissue types. Sixth, spatial-location cues are not required. There is no need, when using methods of the present invention, to know where pixels are located relative to anatomic landmarks; the methods are designed to recognize differences in image intensity alone, without regard to image shape.

Preferred Embodiments

The present invention includes a method of estimating tissue volumes in a pixelized magnetic resonance image, the method comprising: providing magnetic resonance images including pixel gray scale values; selecting a current centroid of a cluster representing each tissue; computing a Euclidean distance from each pixel vector to each current centroid; computing a membership value for each pixel vector in each cluster; computing a new centroid for each cluster; returning to the step for computing Euclidean distance after substituting the new centroid for the current centroid for each cluster if testing reveals insufficient convergence due to separation of the new and current centroids for each cluster greater than a desired threshold (preferably about 0.1); and computing tissue volumes based on pixel vector membership values.

The present invention also comprehends non-iterative techniques. For example, a method of estimating tissue volumes in a magnetic resonance image, the method comprising: providing a magnetic resonance image including pixel gray scale values, the values being obtained from proton density (PD) and T2-weighted magnetic resonance images and, in some embodiments, from a T1-weighted magnetic resonance image; selecting a current centroid of a cluster representing each tissue; computing a Euclidean distance from each pixel vector to each current centroid; computing a membership value for each pixel vector in each cluster; and estimating tissue volumes based on pixel vector membership values by summing up and averaging membership values to compute tissue volumes.

The present invention also includes a method of operating a machine to estimate tissue volumes in a magnetic resonance image, the machine comprising a processor operatively connected to a memory, the method comprising: selecting a current centroid of a cluster representing each tissue; storing the current centroid of each cluster in the memory; storing a magnetic resonance image including pixel gray scale values in the memory; computing with the processor a Euclidean distance from each pixel vector to each current centroid; computing with the processor a membership value for each pixel vector in each cluster; computing with the processor a new centroid for each cluster; returning to the step for computing Euclidean distance after substituting in the memory the new centroid for the current centroid for each cluster if testing with the processor reveals insufficient convergence due to separation of the new and current centroids for each cluster greater than a desired threshold (preferably about 0.1); and estimating with the processor tissue volumes based on pixel membership values.

The present invention also includes a program storage device readable by a machine, tangibly embodying a program of instructions executable by the machine to perform the method steps of the invention.

A further embodiment of the invention is a method of estimating a volume of brain tissues in a patient, comprising: providing a magnetic resonance image of a patient's brain tissues; estimating a volume of gray matter in the image using a fuzzy clustering process; estimating a volume of white matter in the image using a fuzzy clustering process; and estimating a volume of cerebrospinal fluid in the image using a fuzzy clustering process.

Clinical applications of the present invention include a method of diagnosing hydrocephalus in a patient, comprising: providing a magnetic resonance image of a patient's brain tissues; estimating a volume of cerebrospinal fluid in the image using a fuzzy clustering process; and diagnosing hydrocephalus if estimated cerebrospinal fluid volume is greater than a predetermined percentage of about ten percent, the actual value depending on the location of the image plane in the brain.

Another clinical application of the present invention is a method of diagnosing hydrocephalus in a patient, the method comprising: providing magnetic resonance images of a patient's brain tissues including pixel gray scale values; selecting a current centroid of a cluster representing gray matter; selecting a current centroid of a cluster representing white matter; selecting a current centroid of a cluster representing cerebrospinal fluid; computing a Euclidean distance from each pixel vector to each current centroid; computing a membership value for each pixel vector in each cluster; computing a new centroid for each cluster; testing for separation of new and current centroids for each cluster; substituting the new centroid for the current centroid for each cluster; returning to the step for computing Euclidean distance if testing reveals separation greater than a desired error; estimating tissue volumes based on pixel vector membership values; and diagnosing hydrocephalus if cerebrospinal fluid volume is greater than a predetermined percentage of about ten percent, the actual value depending on the location of the image plane in the brain.

Another embodiment of the present invention is apparatus for estimating tissue volumes in magnetic resonance images, the apparatus comprising: a magnetic resonance unit for producing pixelized magnetic resonance images; a memory for storing the pixelized images; program storage for central processing unit programs; a central processor unit to perform the steps of: selecting a current centroid of a cluster representing each tissue; storing the current centroid of each cluster in the memory; storing a magnetic resonance image including pixel gray scale values in the memory; computing with the processor a Euclidean distance from each pixel vector to each current centroid; computing with the processor a membership value for each pixel vector in each cluster; computing with the processor a new centroid for each cluster; testing with the processor for separation of new and current centroids for each cluster; substituting in the memory the new centroid for the current centroid for each cluster; returning to the step for computing Euclidean distance if testing reveals separation greater than a desired error; and estimating with the processor tissue volumes based on pixel vector membership values; a display to present gray scale data representing pixelized magnetic resonance images to an operator; and an interface to transfer pixelized magnetic resonance image data from a computation bus to a display and to transfer operator instructions to a central processor unit via a computation bus.

DETAILED DESCRIPTION

Preprocessing of Pixelized MR Image Data

Figure 1:
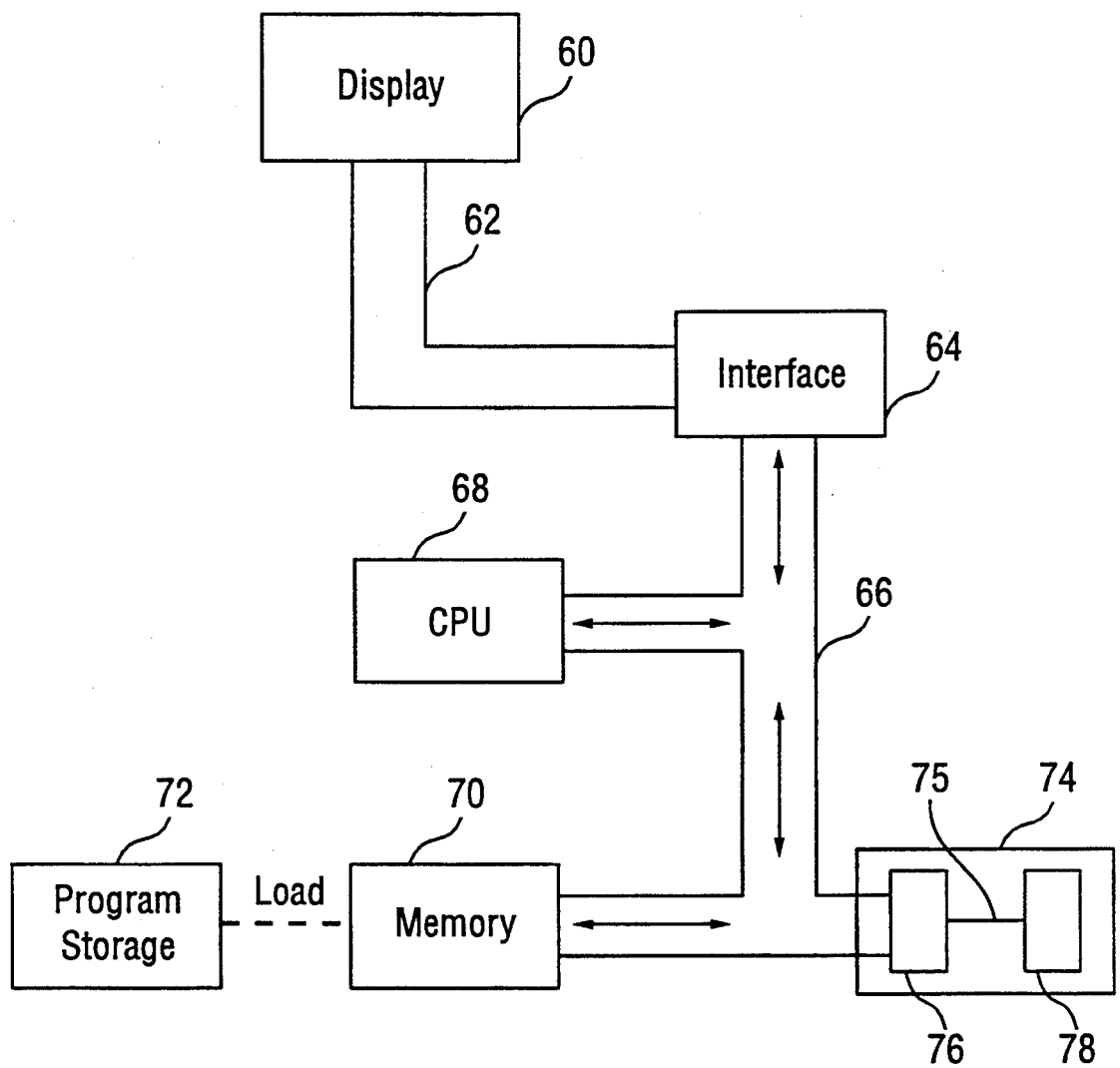
FIG. 1 is a block diagram of hardware components comprising an apparatus for estimating tissue volumes in MR images according to the present invention.

Preferred embodiments of the present invention comprise applications of data preprocessing steps 17 and 18 (see FIG. 2 and computer code printout below), followed by fuzzy clustering 19 of the remaining data. Referring to the apparatus illustrated in FIG. 1, preprocessing is applied to data from pixelized MR images which are produced in MR unit 74 (e.g., General Electric Signa Magnetic Resonance Imaging System) and stored in the memory 70 (which may comprise, e.g., magnetic memory media and volatile or non-volatile semiconductor memory). MR unit 74 comprises MR image section 78 which produces MR images, and MR interface section 76 which receives MR image data over MR internal bus 75 from MR image section 78. MR interface section 76 produces and archives to memory (with a file directory) pixelized MR images in a format usable in methods of the present invention.

Working through the interface 64 (e.g., a keyboard), a human operator can observe data transmitted to the display 60 (e.g., an SVGA monitor) over display path 62 and visually determine a threshold, which effectively determines the characteristic of a highpass filter through which pixelized MR image data are passed. Application of the filter will eliminate substantially all of the noise in the MR image data.

Alternatively, this process can be performed by the central processing unit (CPU) 68 (e.g., an 80486, 33 MHz computer) using a thresholding program drawn from memory 70 over computation bus 66, the program having been previously loaded into memory 70 from program storage media 72.

Program storage media 72 may be, for example, magnetic media including tape, disc or drum, semiconductor media such as semiconductor read only memory, optoelectronic media such as a CD ROM, mechanical storage media such as punched cards, or any other information storage media which is capable of storing a program of instructions that may be executed by the apparatus of FIG. 1 to perform the methods of the present invention.

Figure 2:
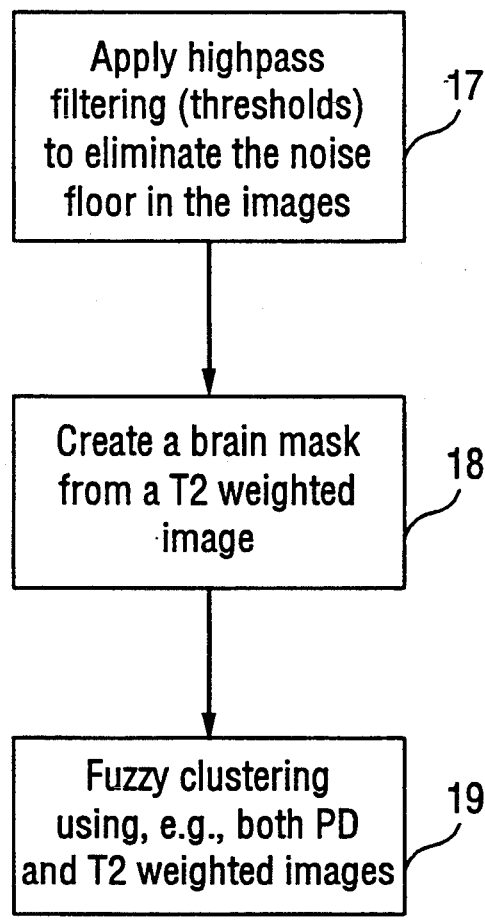
FIG. 2 is a flow chart of the operation of the apparatus of FIG. 1 showing data preprocessing followed by a fuzzy clustering of tissue types in MR images in accordance with the present invention.

As illustrated in FIG. 2, preprocessing also comprises thresholding 17 (see computer code subroutine Hi__Threshold__Image( )) and treating a brain mask 18 (see computer code subroutine Fill__Brain( )) from a T2 weighted image to simplify application of the fuzzy clustering process 19 (see computer code subroutine Cluster( )). Methods of the present invention include the above preprocessing steps because of the requirement for a high signal-to-noise (S/N) ratio in digital MR image data applied to the fuzzy clustering process.

Figure 5A:
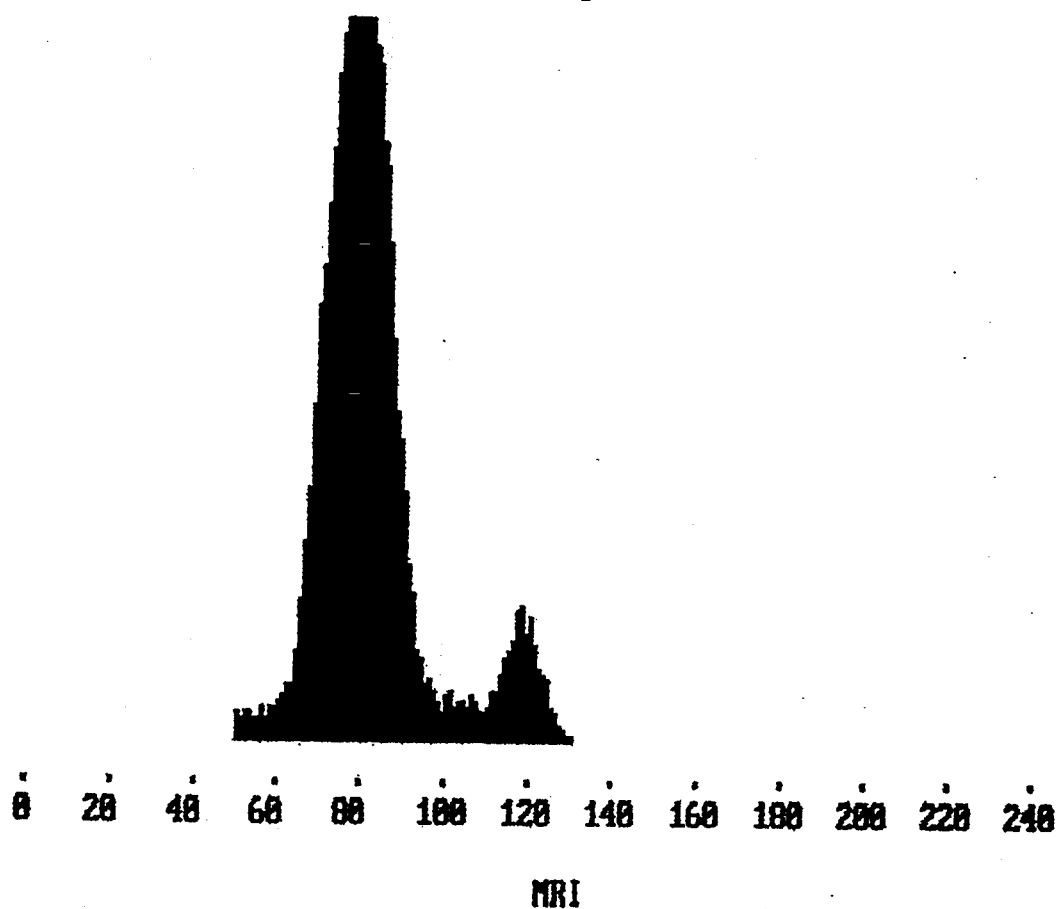
FIG. 5A displays an example of the threshold that would be selected by the operator for a typical PD-weighted axial MR image.
Figure 5B:
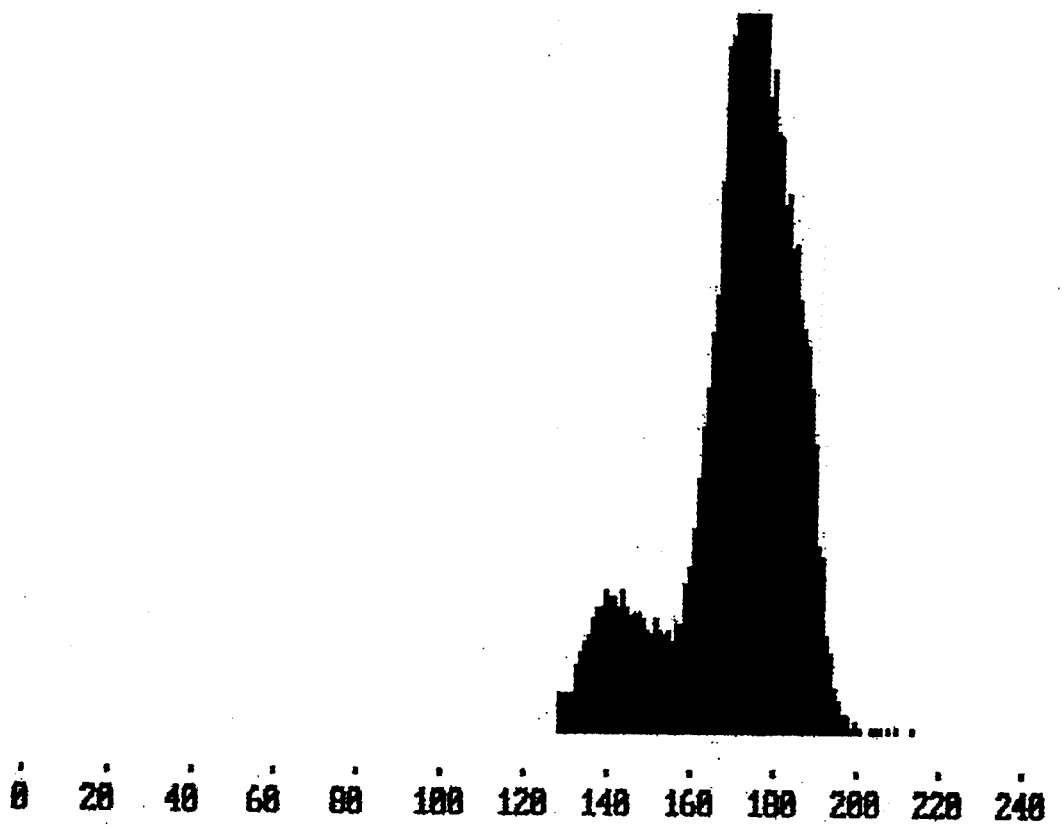
FIG. 5B displays an example of the threshold that would be selected by the operator for a typical T2-weighted axial MR image.

Thresholding is performed interactively by the operator as the gray scale histogram of each slice image is viewed individually. The operator selects a threshold at a point in the histogram just before the beginning of the cerebral density distribution of the data. FIGS. 5A and 5B display examples of the thresholds that would be selected by the operator for a typical PD-weighted (5A) and T2-weighted (5B) axial MR image. Preprocessing is applied individually to the PD and T2-weighted MR images and to any other image (spectral channel) available for each tissue slice to be considered (e.g., a T1-weighted image in certain embodiments).

Creating a Brain Mask

Figure 6A:
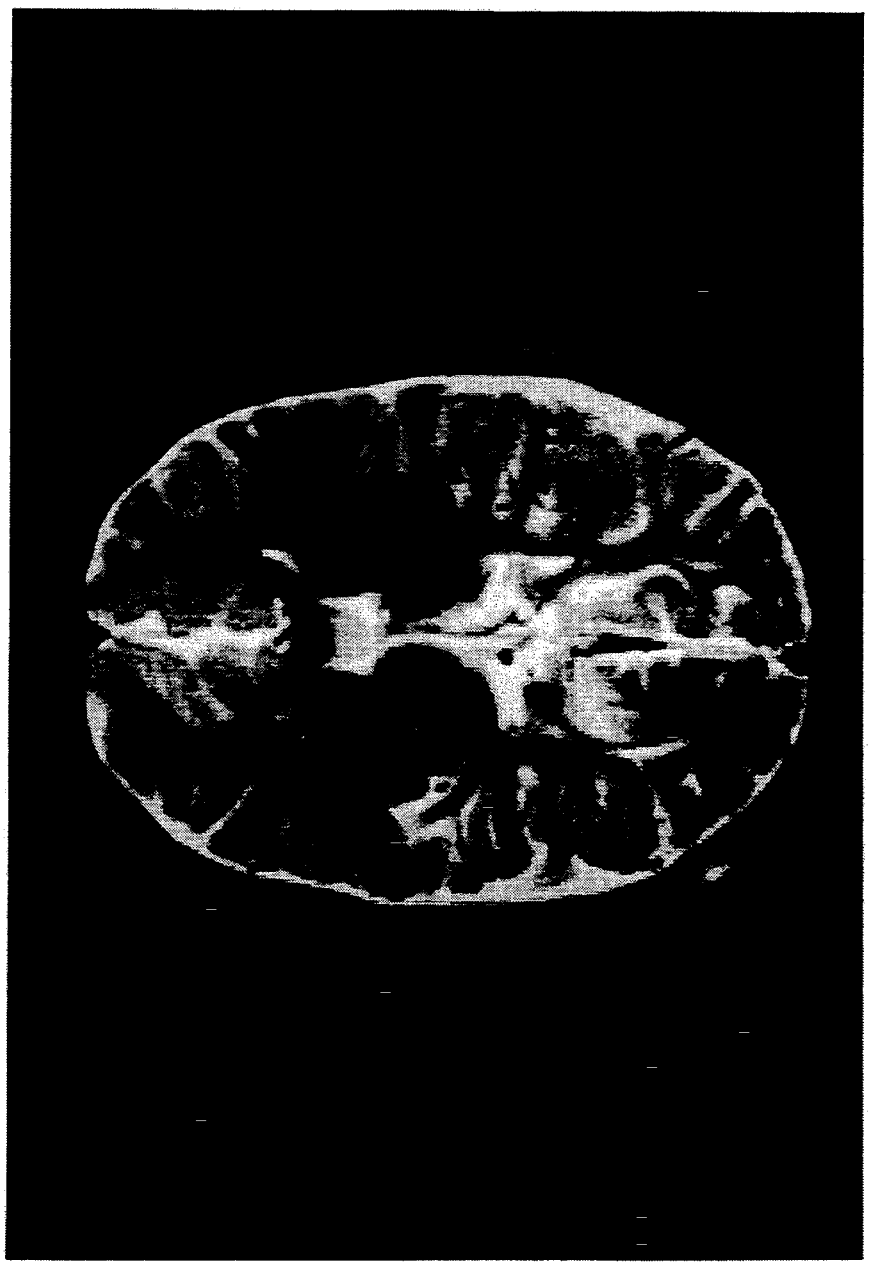
FIG. 6A shows a photograph of an example of a filtered T2-weighted image.
Figure 6B:
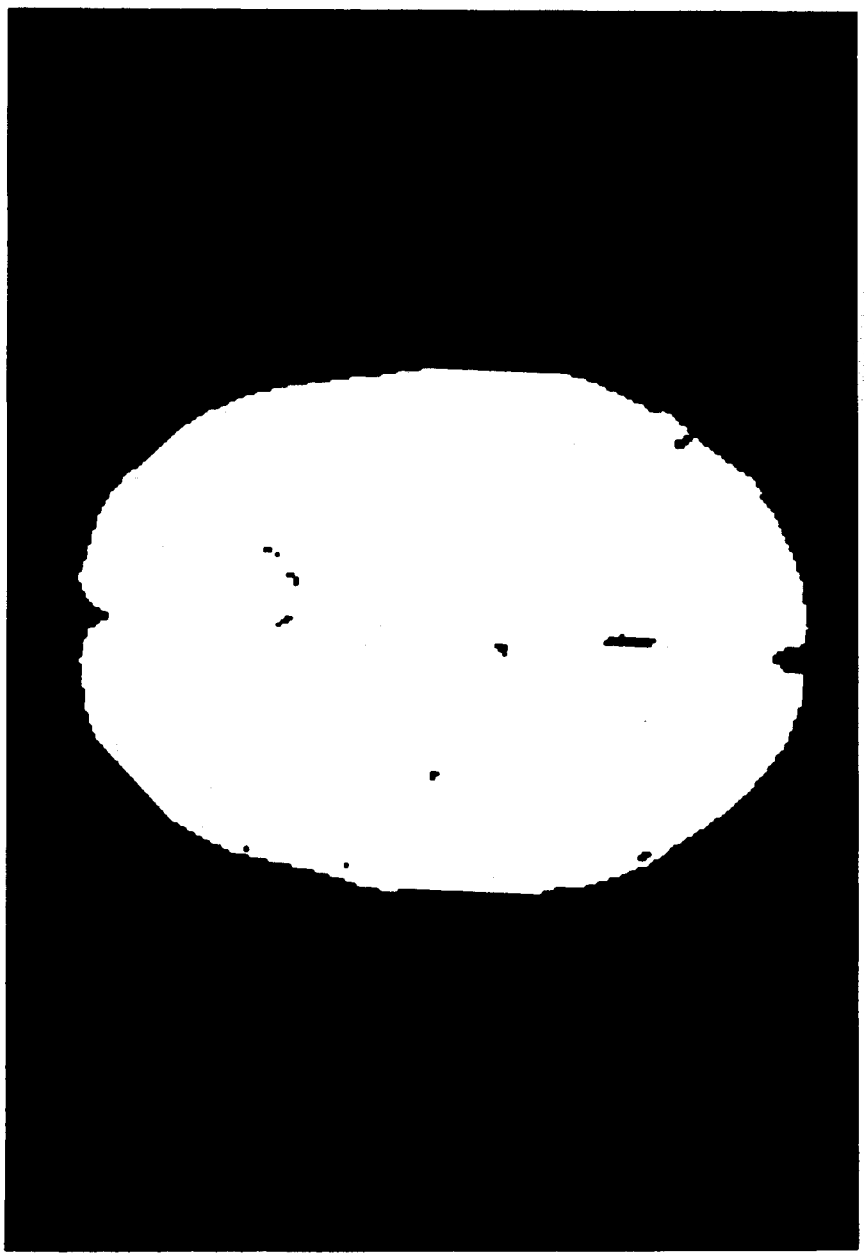
FIG. 6B shows a photograph of an example of the mask produced from the filtered T2-weighted image of FIG. 6A.
Figure 6C:
FIG. 6C shows a photograph of an example of a solution image showing the final classification of each pixel in the T2-weighted image of FIG. 6A and its corresponding PD-weighted image (not shown), calculated using the mask of FIG. 6B.

Following highpass thresholding of the T2-weighted axial image, the cerebrum will have been isolated from skull, meninges, and scalp. A brain mask is then created by using a polygon filling subroutine (subroutine Fill__Brain( )) to isolate all nonzero pixels within the cerebrum itself (pixels of zero gray scale are not filled). The filling algorithm is a region growing procedure that starts from the middle of the image and scans outward in all directions to find all nonzero pixels. FIGS. 6A, 6B and 6C show photographs of examples of a filtered T2-weighted image (6A), the mask produced from it (6B) and the solution image (6C) showing the final classification of each pixel. The brain mask is used to identify all pixel locations to be included in the actual fuzzy clustering procedure. The maximum number of pixels included in the procedure is generally about one-third of the total number present (i.e., about 20,000).

The Fuzzy Clustering Process—Choosing Initial Current Centroids

The fuzzy clustering process for the present invention (FIG. 3 and step 19 in FIG. 2) requires an initial guess as to the gray scale values that characterize the white, gray and CSF compartments in the image. These guesses represent the choice of current (initial) centroid vector 30 or the most representative gray scale Value for the pixels of each cluster, each cluster representing one of the compartments of the image (e.g., a tissue type). The final solution has been observed in repeated tests to be independent of the choice of initial current centroid values, but initial values substantially different from final centroid values tend to increase the computation time required. Thus, the following strategy is used in selecting initial centroid vectors automatically.

For the PD-weighted image, the histogram is computed and its range is quantified (high end minus low end); the range is divided into three substantially equal parts. The approximate center of the lowest third portion of the histogram is designated as the CSF centroid value. The approximate center of the middle third portion is designated as the white matter centroid value, and the approximate center of the highest third portion is deemed the gray matter centroid value. A similar procedure is carried out for the histogram of the corresponding T2-weighted image (the range being divided into three substantially equal parts). The approximate center of the lowest third of the histogram is assigned to white matter, the approximate center of the middle third is designated as gray matter and the approximate center of the highest third is designated as CSF. Centroid vectors are them constructed as the PD and T2 paired values of CSF, white and gray matter as chosen. The portions of each histogram chosen to represent the initial guesses for CSF, white and gray matter are based on empirical observations of many PD and T2-weighted brain images by a trained neurologist and neuropsychologist.

The cluster centroids are thus 2-dimensional vectors where the dimensions are the PD and T2-weighted pixel values selected as above. The term "pixel vector" is used to describe a PD and T2 pixel pair at a given spatial location in both PD and T2-weighted images of the same brain slice. Distances between pixel vectors and cluster centroid vectors are thus computed in a 2-dimensional Euclidean space (or in a 3-dimensional space if T1-weighted images are also used).

Figure 3:
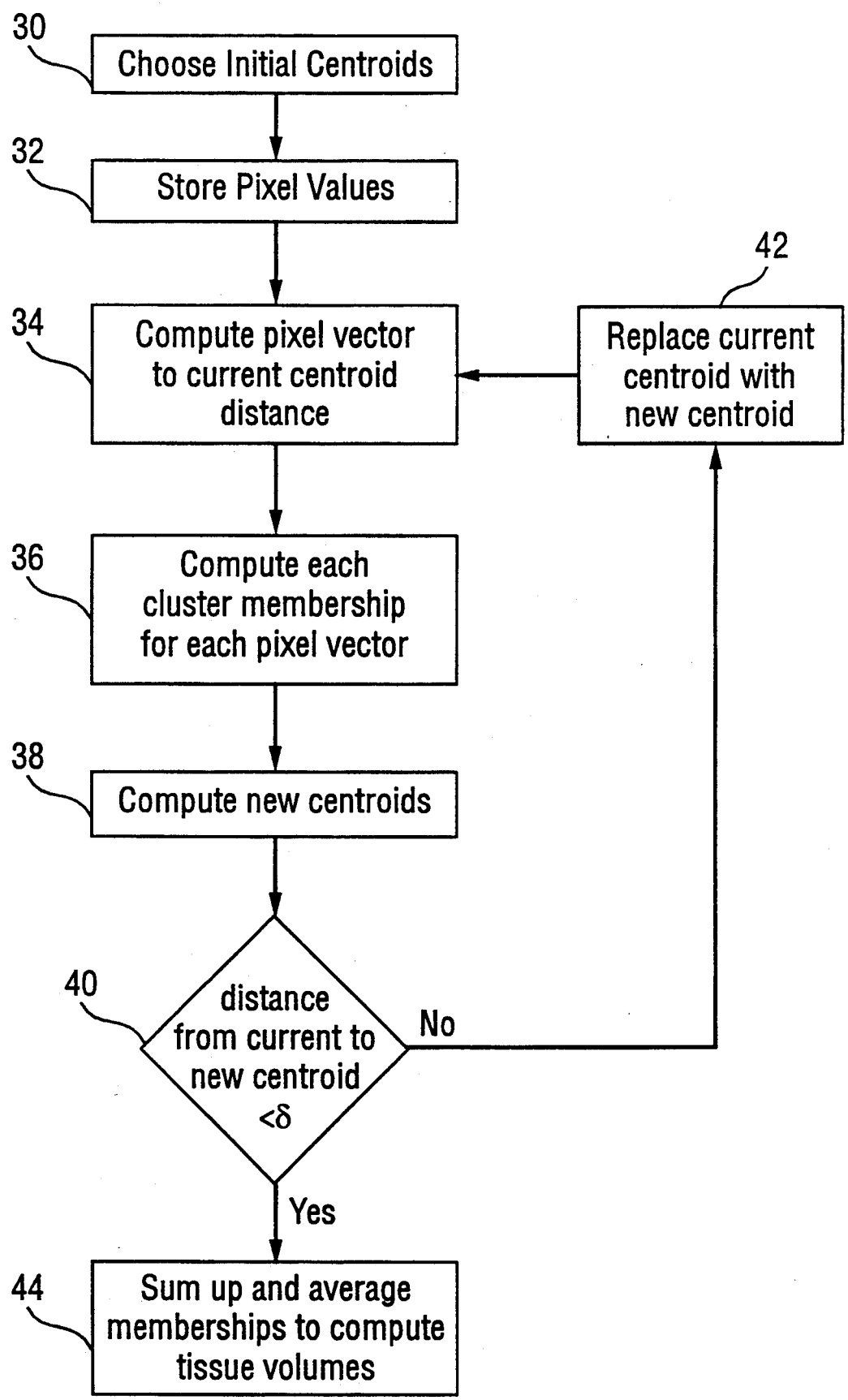
FIG. 3 is a flow chart showing detailed steps in the fuzzy clustering process realized when the apparatus of FIG. 1, operated according to the steps of FIG. 2, is applied to preprocessed MR image data.

Having initially chosen current centroids for the pixel clusters, one must store 32 in some (preferably digital) memory all pixel values to be used in the clustering process (see FIG. 3). Preferred memory includes magnetic discs or tape, optoelectronic or electronic memory. Pixel values needed temporarily for computations may also be stored in random access electronic or optoelectronic storage means linked to a processor.

Using initially chosen current centroid vectors for clusters representing tissue types under consideration, the Euclidean distance of each image pixel vector to each centroid vector is computed 34, and a value representing the membership of each pixel vector in each cluster is also computed 36. The fuzzy clustering procedure thus implemented in the present invention (see FIGS. 2 and 3) is a modified version of an infinite variety of such processes with the general name "fuzzy c-means algorithm" (Bezdek, James, *Pattern Recognition with Fuzzy Objective Function Algorithms*, New York, Plenum Press (1981); and Pao, Yoh-Han, *Adaptive Pattern Recognition and Neural Networks*, Addison-Wesley (1989) ).

More specifically, the fuzzy clustering procedure of the present invention (FIG. 3) comprises the following steps. After choice of initial centroids 30 (see computer code subroutine Cluster( )) and storage of pixel values 32 (see computer code subroutine get_hist( )), the procedure iterates:

1. For each image pixel vector (consisting of PD and T2-weighted gray scale pairs), the squared Euclidean distance 34 to each Cluster centroid vector is computed as $$\mu x_k - v_i \mu^2$$

where $x_k$ refers to each of the n pixel vectors and $v_i$ refers to each of the $N_c$ cluster centroid vectors.

2. Using the previous calculation for distance, the fractional membership 36 of pixel vector k in cluster i is computed as:

$$\mu_{ik} = \frac{\left(\frac{1}{\|x_k - v_i\|^2}\right)^{\frac{1}{m-1}}}{\sum_{j=1}^{N_c} \left(\frac{1}{\|x_k - v_j\|^2}\right)^{\frac{1}{m-1}}};$$

$$i = 1, 2, \ldots, N_c; k = 1, \ldots, n$$

where m is referred to as the "fuzzification parameter" ($1 < m < \infty$). This parameter essentially controls the amount of cluster overlap. The value of m for the present invention has been determined to be about 4/3.

3. The cluster centroid vectors are recalculated 38 using the membership values computed in step 2. The centroid calculation is:

$$v_i = \left(\frac{1}{\sum_{k=1}^{n} (\mu_{ik})^m}\right) \sum_{k=1}^{n} (\mu_{ik})^m x_k; i = 1, \ldots, N_c$$

4. Compute the absolute difference 40 (Euclidean distance) between cluster controids calculated in the present iteration and those calculated in the previous iteration. If this distance exceeds a value $0 < \delta < 0.5$, preferably $\delta = 0.1$, for any cluster, replace the current centroid with the centroid recalculated above 42, then return to step 1 and repeat steps 1–4. Otherwise, convergence in the least mean squares sense has been achieved and the procedure is therefore complete. Finally, the percent volume of the tissue type represented by each cluster is computed 44 as:

$$\left(\left(\sum_{k=1}^{n} \mu_{ik}\right)/n\right) \times 100 \text{ for } i = 1 \text{ to } N_c$$

Note that this procedure utilizes a different convergence criterion than the standard fuzzy c-means algorithm. In the latter, the convergence rule is:

if $max(|\mu_{ik,\alpha} - \mu_{ik,\alpha-1}|) < \delta$ then stop.

where $\mu_{ik,\alpha}$ is the membership of pixel vector k in cluster i for current iteration $\alpha$. This means that the previous iteration's membership matrix (which has dimensionality $N_c$ by n) must be retained (stored in memory) during the current iteration, and the $N_c$ by n absolute differences between the current iteration's membership matrix and the previous one must be computed and the maximum difference determined. Note also that steps 34, 36, 38, 40, 42 and 44 above are represented in the computer code subroutines mem_sqr( ) and fuzzcmns( ) which are listed below.

In the present invention, the $N_c$ absolute differences are only calculated between the current iteration's cluster centroid vectors and the previous iteration's centroid vectors; the maximum difference is then found. This represents a large saving in memory space and computation time over the usual fuzzy c-means algorithm.

Use of the centroid difference approach over the membership difference approach is justified by noting that they are procedurally interchangeable. That is, stability of membership values is reflected in stable positioning of the cluster centroids.

For the clinical tests described herein, the value of $\delta = 0.1$ for the distance threshold was chosen after many empirical tests of the procedure on normal and hydrocephalic children. This value represents 1/10 of one gray scale unit. If it is assumed that there are at most about 10,000 to 12,000 pixel vectors in a given cluster, then the average error per pixel vector would be on the order of 0.1/10,000 (0.00001) to 0.1/12,000 (0.0000083). This allows a highly accurate determination of cluster centroid locations and membership values. Experimental results have shown that a threshold of about $\delta = 0.1$ is an acceptably small error, allowing detection of clinically meaningful differences between normals and hydrocephalics.

Following the percentage computation of CSF, white and gray matter, a solution image is constructed in order to provide some verification of the accuracy of the procedure. The final centroid vectors are deemed the most representative prototypical values for each tissue type. The T2 values of these vectors are used to construct the solution image by multiplying the membership values of each tissue type by the T2 gray scale values for each centroid and then summing:

new gray scale value $= A + B + C$ where
 $A = \text{mem}\{csf\} * \text{centroid}\{csf\}$
 $B = \text{mem}\{white\} * \text{centroid}\{white\}$
 $C = \text{mem}\{gray\} * \text{centroid}\{gray\}$
and
the mem{ } values are the membership percentages computed for each T2-weighted gray scale value in the original image, and the centroid { } values are the final cluster centroid positions in the T2 space. Finally, this "defuzzified" solution image is displayed simultaneously with the PD, T2 and mask images for visual comparison by a trained neurologist on neuroradiologist.

Determining the Fuzzification Parameter

Use of the process requires a choice for a parameter "m," determining the amount of fuzziness of the classification of each pixel. Theoretically, one may choose $1 < m < \infty$, but in analyzing MR images, $1 < m \leq 2$ has been found preferable, with a value of m about 4/3 being most preferred.

The estimated tissue volumes finally computed are dependent on the chosen value of m. There are no guidelines in the literature for selecting the proper value in the present application, although a value for m of 1.3 has been used in other applications. The optimal value appears to depend to a certain extent on the problem domain (e.g., MR image processing) and the data. There are, however, some important guidelines for determining the optimal m for any given application. The idea is represented by the diagram of FIG. 4, illustrating the membership percentage (vertical axis) for two hypothetical gray scale pixel clusters, c1 and c2.

Figure 4:
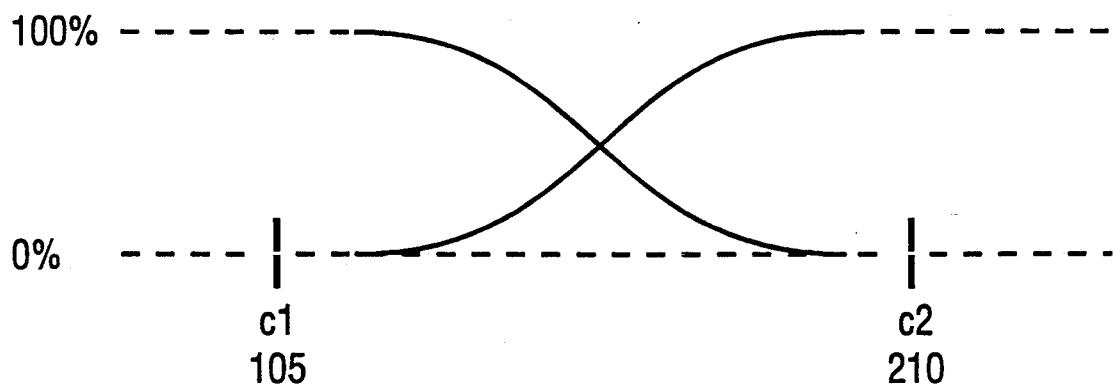
FIG. 4 illustrates the membership percentage (vertical axis) for two hypothetical gray scale pixel clusters.

In FIG. 4, the horizontal axis represents increasing gray scale values with the centroid value for $c1 = 105$ and for $c2 = 210$. The parameter m should be selected in such a way that gray scale values to the left of c1 should have 100% membership with the c1 cluster, and 100% membership to the right of c1 up to a point where the membership values begin to decrease. Eventually the membership values for c1 will decrease more or less smoothly to 0%. For c2, gray scale values to the right of 210 should belong 100% to the c2 cluster, with a similar falloff in values to the left of c2. At a point approximately halfway between the c1 and c2 values (about 157), the membership for a given gray scale value should be approximately 50—50.

With this objective in mind, numerous tests over many images were performed by trying out different values for m and examining the membership values for each gray scale value in each image. The value 4/3 for m yielded the desired result in every image tested. Slight variations in this value (about 1.2 to 1.4) were observed to make minimal difference in the final estimates of tissue volumes. Further, once chosen, this parameter does not have to be selected or changed by the operator. We finally set the value of m to 4/3, which then yields considerable savings in computation time (see equations in steps 2 and 3 above).

Convergence of the Fuzzy Clustering Process

In tests on actual MR images, the fuzzy clustering process (FIG. 3) always converged to a solution, but the solution was sometimes incorrect if the centroid values for two different tissue types were too close in value. This occurred when one of the three tissue types considered (the fluid compartment) was present as a very small percentage of the total tissue. The process was then unable to distinguish the fluid compartment and split the gray matter cluster into two separate clusters. This error is eliminated by modifying the thresholding step to eliminate any one of the tissue types, followed by subtracting the thresholded image from the original. The remaining image, which contains only the remaining two tissue types, may then be subjected to the procedure and the two-cluster solution found.

Clinical Tests of the Process

An MR image analysis comparing three clinically normal control children with three age matched hydrocephalic children reveals the clinical utility of the present invention. The results are summarized in Table I (all listed results use $m = 1.3$, but a value of $m = 4/3$ is preferred in embodiments requiring substantial calculational efficiency). In the hydrocephalic group, one subject was born prematurely and was diagnosed as hydrocephalic, and the remaining two were diagnosed as having spina bifida with hydrocephalus. For each subject, three contiguous axial image slices were obtained, proceeding superiorly from a slice through both the genu of the corpus callosum and the lateral ventricles, and including the internal capsule, caudate nucleus and putamen comparison of a total of 36 images for the two groups (6 subjects × 3 image slices per subject × 2 channels [PD and T2]), with volumetric results averaged across the three slices for each subject, is summarized in Table I.

TABLE I

PRELIMINARY RESULTS SYNOPSIS
(All subjects 7 years of age)

| Subject | % CSF | % White | % Gray | White/Gray |
|---------|-------|---------|--------|------------|
| Controls | | | | |
| 1 | 5.3 | 45.0 | 49.7 | 0.91 |
| 2 | 2.4 | 47.4 | 50.2 | 0.94 |
| 3 | 4.5 | 49.4 | 46.1 | 1.07 |
| Mean | 4.1 | 47.3 | 48.7 | 0.97 |

TABLE I-continued
PRELIMINARY RESULTS SYNOPSIS
(All subjects 7 years of age)

| Subject | % CSF | % White | % Gray | White/Gray |
|---------|-------|---------|--------|------------|
| Hydrocephalus | | | | |
| 1 (PH) | 14.5 | 29.0 | 56.5 | 0.51 |
| 2 (SH) | 15.4 | 35.3 | 49.3 | 0.72 |
| 3 (SH) | 17.6 | 35.5 | 46.6 | 0.81 |
| Mean | 15.8 | 33.3 | 50.8 | 0.68 |

Overall, the results indicate the expected finding that the ratio of white matter to gray matter in hydrocephalic children is much lower than that of controls. The results also show the increased amount of brain fluid characteristic of hydrocephalus. But more important, the procedure is able to demonstrate that hydrocephalus severely affects the amount of white matter while sparing the gray matter in general. Specifically, hydrocephalus subject number one had asymmetrical and dilated ventricles and, as expected, a more severe white matter decrease as compared to the other two subjects. Hydrocephalus subject number two had symmetrical, non-dilated ventricles, and thus, less of a decrease in white matter. In summary, the procedure is able to clearly identify gross changes in white, gray and fluid compartments in hydrocephalus.

```
/* MRI System using VICTOR LIBRARY
     M. Brandt, Revision
       1/6/93
*/ include <vicdefs.h>    /* Necessary and useful Victor definitions */
include <vicfcts.h>    /* Victor function declarations */
#include <vicerror.h>   /* Victor error codes */
#include <vicdemo.h>    /* VICDEMO function declarations */
#include <keydefs.h>    /* Key code definitions for getkey() */
include <fill.h> include <stdio.h>
include <stdlib.h>
#include <stdarg.h>
#include <string.h>
#include <io.h>
#include <conio.h>
#include <fcntl.h>
#include <dos.h>
#include <bios.h>
#include <signal.h>
#include <math.h>
#include <time.h>

/*#include "mrib.c"
  */ define   VERBOSE  1      /* If 1, display memory allocation info */
define   CGA_     6      /* Video display modes */
#define   MDA_     7
#define   EGA_     16
#define   EEGA_    18
#define   VGA_     19
#define   NO_VIDADAP -36  /* Local error code */
#define   NC 3

/*-------Global Variables------*/
imgdes Image, Oper, Oper2, Result, desimg;           /* Our primary image buffer */
int ImgWidth = 256;       /* Default buffer dimensions */
int ImgLength = 256;
UCHAR Paldata[768];       /* Palette data buffer */
char Txtbuf[80];          /* General purpose text buffer */
DispHwd Vflags;           /* Reserbe space for video adapter struct */
/*----------------------------*/
union REGS regs;

/* prototypes */ void SetWhite(void);
void ResizeImage2(void);
void Copy_Buffer(void);

int _cdecl showhisto2(int vmode, long *his_table, char *titlestr,
        char *legendstr, int bar_col, int txt_col, int bck_col, int st, int no);

void LoThreshold_Image(void), Threshold_Image(void), HiThreshold_Image(void);

void ex_func(int val);

void Log_Image(void), Add_Image(void), Sub_Image(void), And_Image(void),
     Or_Image(void);
```

```c
void make_palette(UCHAR *data);

UINT gethist(imgdes *src1_image, imgdes *src2_image, imgdes *mask_image,
             UCHAR *x, UCHAR *y);

void fuzzcmns(imgdes *src1_image, imgdes *src2_image, imgdes *mask_image,
              double m, int nc, int no, UCHAR *x, UCHAR *y, UCHAR **mem);

void fuzzprob(imgdes *src1_image, imgdes *src2_image, imgdes *mask_image,
              double m, int nc, int no, UCHAR *x, UCHAR *y, UCHAR **mem);

void Cluster(void);
void Fill_Brain(void);
void Make_Big(void);
void ReadTif(void);
void WriteTif(void);
void Negate(void);

UCHAR **calloc_2d_uc(int rows, int cols);
UINT **calloc_2d_uint(int rows, int cols);

/* fill functions */ void fill_image_line(imgdes *im, UINT xl, UINT y, UINT xr, UINT color);
UINT find_pel(imgdes *im, UINT x, UINT y, UINT lo_color,
        UINT hi_color, UINT match_type);
UINT rightborder (imgdes *im, UINT x, UINT y);
UINT leftborder (imgdes *im, UINT x, UINT y);
UINT out_color(UINT lo, UINT x, UINT hi);
UINT paint_line(imgdes *src, imgdes *dst);
UINT floodfill(imgdes *src, imgdes *dst, UINT x, UINT y);

/*static set_video_mode(int mode_n);

extern MOUSE_STATE near mouse_state;
*/ int save[20];

double cc1[NC][2];

int vmode, pflag;

void main(int argc, char **argv)
{
    int i, j, k, rcode, width, length, fhr;

atexit(exitprog); /* Make sure we release any allocated image buffers */
    signal(SIGINT, SIG_IGN);    /* Ignore ctrl-C's */
    /* Allocate a 64Kb buffer to give us something to work with.
       This buffer will be expanded, if necessary to accomodate
       larger images that are read in.
    */ zeroimgdes(&Image);      /* Zero image descriptor */
    zeroimgdes(&Result);     /* Zero image descriptor */
    zeroimgdes(&desimg);     /* Zero image descriptor */
    zeroimgdes(&Oper);       /* Zero image descriptor */
    zeroimgdes(&Oper2);      /* Zero image descriptor */

/* Try to allocate buffer */ if(mem_alloc(&Image, ImgWidth, ImgLength) != NO_ERROR) {
       errmsg("\n\r Not enough memory to run demo *");
       exit(1);
       } if(mem_alloc(&Result, ImgWidth, ImgLength) != NO_ERROR) {
       errmsg("\n\r Not enough memory to run demo *");
       exit(1);
```

```
          } if(mem_alloc(&Oper, ImgWidth, ImgLength) != NO_ERROR) {
          errmsg("\n\r Not enough memory to run demo ");
          exit(1);
          } if(mem_alloc(&Oper2, ImgWidth, ImgLength) != NO_ERROR) {
          errmsg("\n\r Not enough memory to run demo ");
          exit(1);
          } if(mem_alloc(&desimg, 2*ImgWidth, 2*ImgLength) != NO_ERROR) {
          errmsg("\n\r Not enough memory to run demo ");
          exit(1);
       }

/* Any palette data will be stored in Paldata buffer */

Image.palette = Paldata;
       Result.palette = Paldata;
       desimg.palette = Paldata;

Oper.palette = Paldata;
       Oper2.palette = Paldata;

/* set palette to 256 grey scales */ pflag = 0;

for(j=0; j<3*256; j++)
             Paldata[j] = (UCHAR)(j / 3);

/* point */

/* Clear the image buffer */
       if((rcode=zeroimage(0, &Image)) != NO_ERROR)
             error_handler(rcode);     /* Handle any errors */
       if((rcode=zeroimage(0, &Result)) != NO_ERROR)
             error_handler(rcode);     /* Handle any errors */
       if((rcode=zeroimage(0, &Oper)) != NO_ERROR)
             error_handler(rcode);     /* Handle any errors */
       if((rcode=zeroimage(0, &Oper2)) != NO_ERROR)
             error_handler(rcode);     /* Handle any errors */
       if((rcode=zeroimage(0, &desimg)) != NO_ERROR)
             error_handler(rcode);

/*     pause();
 */ pcvideoinfo(&Vflags);     /* Set PC display adapter flags */ if(strcmp(argv[1], "para")) vmode = 0x5f;
       else vmode = 0x5d;     /* trident */ if(argc == 3) {

/* Make sure file exists and get its length */ if((fhr=open(argv[2], O_BINARY|O_RDONLY)) < 3)
             rcode = BAD_OPN;
          else {
          /* File opened, set image width, calc image length */
          width = ImgWidth;
          length = (int)(filelength(fhr) / width);
          close(fhr);
          /* Resize the image buffer to the file dimensions */
          rcode = resiz_imgbuf(&Image, width, length);
          if(rcode != NO_ERROR)
             printf("\nNot enough memory to load entire image."
                   "\nImage is: %d x %d, Buffer is: %d x %d",
                   width, length, Image.iwidth, Image.ilength);
```

```c
        printf("\nReading binary file %s...", argv[2]);
        rcode = loadbif(argv[2], &Image);
        }
        if(rcode != NO_ERROR)    /* Display any error messages */
            error_handler(rcode, argv[2]);

}

/*  set_video_mode(1);
    reset_auto_cs_layout(0);

mouse_show_crsr();
    pause();
    mouse_hide_crsr();
    */ select_function();

} void make_palette(UCHAR *data)
{
    int i, j, k;

if(pflag) { pflag = 0;

for(j=0; j<3*256; j++)
                data[j] = (UCHAR)(j / 3);
    } else {
            pflag = 1;

/* to cyan */ for(j=k=0; j<32; j++) {
        i = j*8;
        data[k++] = 0;
        data[k++] = 0;
        data[k++] = i;
    } for(j=0; j<32; j++) {
        i = j*8;
        data[k++] = 0;
        data[k++] = i;
        data[k++] = 248;
    }

/* to yellow */ for(j=0; j<64; j++) {
        i = j*4;
        data[k++] = i;
        data[k++] = 252;
        data[k++] = 252 - i;
    }

/* to red */ for(j=0; j<64; j++) {
        i = j*4;
        data[k++] = 252;
        data[k++] = 252 - i;
        data[k++] = 0;
    }

/* to black */ for(j=0; j<64; j++) {
        i = j*4;
        data[k++] = 252 - i;
        data[k++] = 0;
        data[k++] = 0;
```

```
    }
    data[765] = data[766] = data[767] = 255;

}

/*  increase to blue for(j=k=0; j<64; j++) {
        i = j*4;
        data[k++] = 0;
        data[k++] = 0;
        data[k++] = i;
    } get to cyan for(i=0, j=32; j<64; j++, i++) {
        data[k++] = 0;
        data[k++] = i*8;
        data[k++] = 252;
    } get to green for(j=0; j<32; j++) {
        data[k++] = 0;
        data[k++] = 252;
        data[k++] = 248 - j*8;
    } on to yellow for(i=0, j=32; j<64; j++, i++) {
        data[k++] = i*8;
        data[k++] = 248;
        data[k++] = 0;
    } on to red for(j=0; j<32; j++) {
        data[k++] = 248;
        data[k++] = 248 - j*8;
        data[k++] = 0;
    } to black for(j=0; j<64; j++) {
        data[k++] = 252 - j*4;
        data[k++] = 0;
        data[k++] = 0;
    }

---------- for(j=0; j<32; j++) {
        data[k++] = 248;
        data[k++] = 0;
        data[k++] = 248 - j*8;
    } for(j=0; j<32; j++) {
        data[k++] = 248 - j*8;
        data[k++] = 0;
        data[k++] = 0;
    }

*/

}
```

```c
/* Choose a function */
void select_function(void)
{
    int val, endflag=0;
    int i, n=0, rflag=0;

while(endflag==0) {
        show_menu();
top:    val = getkey();            /* Wait for a key (no screen echo) */
        if(inrange(' ',val,'~'))   /* inrange() is defined in vicdefs.h */
            fputc(val, stdout);    /* Display char if ' '->'~' */ if(rflag) {
            if(n < 19) {
                n++;
                save[n]=val;
            }
        } switch(val) {
            case '2': WriteBif(); break;
            case '1': ReadBif(); break;
            case 'a': case 'A': Blur_Image(); break;
            case 'b': case 'B': Change_Bright(); break;
                case 'c': case 'C': Exchange_Gray(); break;
            case 'd': case 'D': Kodalith_Image(); break;
            case 'e': case 'E': Expand_Contrast(); break;
            case 'f': case 'F': LoThreshold_Image(); break;
            case 'g': case 'G': Gentle(); break;
            case 'h': case 'H': DispHisto(); break;
            case 'i': case 'I': Pixellize_Image(); break;
            case 'j': case 'J': Divide_Image(); break;
            case 'k': case 'K': Multiply_Image(); break;
            case 'l': case 'L': Linearize(); break;
            case 'm': case 'M': Copy_Buffer(); break;
            case 'n': case 'N': Add_Image(); break;
            case 'o': case 'O': HiThreshold_Image(); break;
            case 's': case 'S': HipassFilter(); break;
            case 't': case 'T': Trace_It(); break;
            case 'u': case 'U': Display(); break;
            case 'q': case 'Q': endflag = 1; break;
            case 'v': case 'V': ResizeImage2(); break;
            case 'r': case 'P': rflag = 1; n=0; break;
            case 'p': case 'R': for(i=1; i<=n; i++) ex_func(save[i]);
                                break;

case 'w': case 'W': rflag = 0; break;
            case 'x': case 'X': Sub_Image(); break;
            case 'y': case 'Y': And_Image(); break;
            case 'z': case 'Z': Or_Image(); break;
            case '3': Threshold_Image(); break;
            case '4': Cluster(); break;
                case '5': Fill_Brain(); break;
            case '6': Make_Big(); break;
            case '7': WriteTif(); break;
            case '8': ReadTif(); break;
            case '9': make_palette(Paldata); break;
            case '*': Print(); break;
                case '-': Negate(); break;
                default: chirp();  erase_eol(); goto top;
        }
    }
} void Print(void)
{ int d;
    printf("\n\nDPI 150 (1) or 300 (2)? ");
    scanf("%d", &d);

printimage(0, d, &Result, 5, 5, 2005, 2005, 0);

} void ex_func(int val)
{
```

```c
    switch(val) {
        case 'a': case 'A': Blur_Image(); break;
        case 'b': case 'B': Change_Bright(); break;
        case 'c': case 'C': Exchange_Gray(); break;
        case 'd': case 'D': Kodalith_Image(); break;
        case 'e': case 'E': Expand_Contrast(); break;
        case 'f': case 'F': HiThreshold_Image(); break;
        case 'g': case 'G': Gentle(); break;
    case 'h': case 'H': DispHisto(); break;
    case 'i': case 'I': Pixellize_Image(); break;
        case 'j': case 'J': Divide_Image(); break;
    case 'k': case 'K': Multiply_Image(); break;
    case 'l': case 'L': Linearize(); break;
    case 'm': case 'M': Copy_Buffer(); break;
        case 'n': case 'N': Add_Image(); break;
    case 'o': case 'O': LoThreshold_Image(); break;
    case 's': case 'S': HipassFilter(); break;
    case 't': case 'T': Trace_It(); break;
    case 'u': case 'U': Display(); break;
    case 'v': case 'V': ResizeImage2(); break;
    case 'x': case 'X': Sub_Image(); break;
    case 'y': case 'Y': And_Image(); break;
    case 'z': case 'Z': Or_Image(); break;
    case '3': Threshold_Image(); break;
    default: break;

}

} void show_menu(void)
{
    crt_cls();
    puts("\r>> MRI System - Neurosignal Science Analysis Laboratory, U.T. Medical School <<\n");

puts("1. Load binary file                2. Save binary file");
    puts("A. Blur image                      B. Change brightness");
    puts("C. Exchange gray levels            D. Get CSF (by kodalith)");
    puts("E. Expand contrast                 F. Low-Pass Threshold");
    puts("G. Gently sharpen                  H. Display Histogram");
    puts("I. Pixellize                       J. Divide");
    puts("K. Multiply                        L. Linearize");
    puts("M. Copy Buffer                     N. Add Original to Oper");
    puts("O. Hi-Pass Threshold               P. Play sequence");
    puts("R. Record sequence                 S. Sharpen (high pass filter)");
    puts("T. Trace                           U. Display original & Result");
    puts("V. Display large result            W. Stop Recording");
    puts("X. Subtract Oper from Original     Y. AND Original to Oper");
    puts("Z. OR Original to Oper             3. Band-Pass Threshold");
    puts("4. Fuzzy Cluster Analysis          5. Fill brain");
    puts("6. Fill large window               7. Write TIF");
    puts("8. Read TIF                        9. Change Palette");
    puts("-. Negate");
    puts("\nQ. Quit ");

} long total;

void Fill_Brain(void)
{
    long count;
    int rcode;

total = 0;

floodfill(&Result, &Result, 128, 128);
    rcode = kodalith(255, &Result, &Oper);

if(rcode != NO_ERROR)    /* Display any error messages */
        error_handler(rcode);

/*
  blur(&Oper, &Oper);
  exchangegray(1, 255, 255, &Oper, &Oper);
```

```c
    pixelcount(255, 255, &count, &Oper);

printf("\n\nNumber of pixels filled = %d", total);
    printf(   "\nPixel Count             = %d\n", count);

getkey();
      */
} void Cluster(void)
{ int ind, no, val1;
    UINT np;

double third, part, fact;
    double par;
    long his_table[256], pcount;
    int i, j, rcode, low, hi, range;

UCHAR *xx, *yy, **mu;
    FILE *fopen(), *fp;

fp = fopen("hist", "w");

randomize();

cc1[2][0] = cc1[2][1] = 0.0;

printf("\nHow many clusters (2 or 3)?: ");
    scanf("%d", &no);

fprintf(fp, "%d\n", no);

/* get centroid seed values for t1 image */ if((rcode=calchisto(his_table, &Image)) == NO_ERROR) {

/* find low, medium, hi vals for T1 image */ for(low = 0, i=1; i<256; i++)
        if(his_table[i]) {low = i; break;} for(hi = 0, i=255; i>0; i--)
        if(his_table[i]) {hi = i; break;} range = hi - low + 1;
    part = (double)(range/no);
    cc1[2][0] =  (double)low + part/2.0;      /* CSF   */
    cc1[0][0] =  cc1[2][0] + part;            /* white */
 /*  if(no == 3) */
        cc1[1][0] =  cc1[0][0] + part;        /* grey  */

} for(j=0; j<no; j++) fprintf(fp, "%f ", cc1[j][0]);

/* get centroid seed values for t2 image */ if((rcode=calchisto(his_table, &Oper2)) == NO_ERROR) {

/* find low, medium, hi vals for T2 image */ for(low = 0, i=1; i<256; i++)
        if(his_table[i]) {low = i; break;} for(hi = 0, i=255; i>0; i--)
        if(his_table[i]) {hi = i; break;} range = hi - low + 1;
    part = (double)(range/no);
```

```
        cc1[0][1] = low + part/2.0;              /* white  */
        cc1[1][1] =  cc1[0][1] + part;           /* grey   */
        if(no == 3)
              cc1[2][1] =  cc1[1][1] + part;     /* csf */ printf("\nT2 centers ... \n");
        for(i=0; i<3; i++)
            printf(" %.1f ", cc1[i][1]);

} for(j=0; j<no; j++) fprintf(fp, "%f ", cc1[j][1]);

/* get number of pixels in mask */ if((rcode = pixelcount(255, 255, &pcount, &Oper)) != NO_ERROR) {
          error_handler(rcode);
          return;
    }

/*    printf("\nBrain Pixel Area: %d\n", pcount);
*/
    /* allocate space for pixel intensity values & cluster memberships */ if((xx = (UCHAR *)malloc((int)pcount)) == 0) { puts("\nNot enough mem for x\n");
        pause();
        return;
    } if((yy = (UCHAR *)malloc((int)pcount)) == 0) {
        puts("\nNot enough mem for y\n");
        pause();
        return;
    } if((mu = calloc_2d_uc(no, (int)pcount)) == 0) {
        puts("\nNot enough mem for mem\n");
        pause();
        return;
    }

/* obtain number of pixels and intensity values */ np = gethist(&Image, &Oper2, &Oper, xx, yy);
    printf("\nBrain Pixel Area: %u\n", np);

fprintf(fp, "\n%u", np);

for(j=0; j<np; j++)
        fprintf(fp, "\n%d %d", xx[j], yy[j]);

fclose(fp);

/* initialize mu */ val1 = 100/no;

for(j=0; j<no; j++) {
        for(i=0; i<np; i++)
                mu[j][i] = val1;
    } printf("\nEnter m (1.1 --> infinity): ");
    scanf("%lf", &par);

printf("\nFuzzy c-means (1) or fuzzy prob (2)? ");
scanf("%d", &j);
```

```
    if(j == 1) fuzzcmns(&Image, &Oper2, &Oper, par, no, np, xx, yy, mu);
    else       fuzzprob(&Image, &Oper2, &Oper, par, no, np, xx, yy, mu);

free(xx);
    free(yy);
    free(mu);

} void Copy_Buffer(void)

{
    int rcode, val1, val2;

imgdes *a, *b;

/* Get user input, convert to int*/ val1= getnum("\nBuffer to copy (1-4): ");
    if(val1 == -1)    /* -1 => invalid entry */
        return;

val2= getnum("\nCopy to Buffer (1-4): ");
    if(val2 == -1)    /* -1 => invalid entry */
        return;

switch(val1) {
          case 1: a = &Image;  break;
          case 2: a = &Oper ;  break;
          case 3: a = &Result; break;
          case 4: a = &Oper2;  break;
          default: break;
    } switch(val2) {
          case 1: b = &Image;  break;
          case 2: b = &Oper ;  break;
          case 3: b = &Result; break;
          case 4: b = &Oper2;  break;
          default: break;
    } if((rcode = copyimage(a, b)) != NO_ERROR)
        error_handler(rcode);

} void Add_Image(void)
{
   int rcode;

if((rcode=addimage(&Image, &Oper, &Result)) != NO_ERROR)
       error_handler(rcode);

} void Sub_Image(void)
{
   int rcode;

if((rcode=subimage(&Image, &Oper, &Result)) != NO_ERROR)
       error_handler(rcode);

} void And_Image(void)
{
   int rcode;
```

```c
    if((rcode=andimage(&Image, &Oper, &Result)) != NO_ERROR)
       error_handler(rcode);

} void Or_Image(void)
{
  int rcode;

if((rcode=orimage(&Image, &Oper, &Result)) != NO_ERROR)
       error_handler(rcode);

} void Display(void)
{ int j, rcode;

setvideomode(vmode);    /* Paradise */
/*    init_GFX_struct(256);
    mouse_show_crsr();
    pause();
 */ setvgapalette(Image.palette);
    setvgapalette(Result.palette);

/*   setvgapalette(desimg.palette);
 */ setvgapalette(Oper.palette);
    setvgapalette(Oper2.palette);

if(vmode == 0x5d) { if((rcode = viewtridevga(vmode, 0, 0, &Image)) != NO_ERROR) {
       puts("Error in displaying original");
       return;
    } if((rcode = viewtridevga(vmode, 256, 0, &Oper)) != NO_ERROR) {
       puts("Error in displaying oper");
       return;
    } if((rcode = viewtridevga(vmode, 0, 234, &Result)) != NO_ERROR) {
       puts("Error in displaying result");
       return;
    } if((rcode = viewtridevga(vmode, 256, 234, &Oper2)) != NO_ERROR) {
       puts("Error in displaying oper2");
       return;
    }

}
  else { if((rcode = viewparaevga(vmode, 0, 0, &Image)) != NO_ERROR) {
       puts("Error in displaying original");
       return;
    } if((rcode = viewparaevga(vmode, 256, 0, &Oper)) != NO_ERROR) {
       puts("Error in displaying oper");
       return;
```

```c
    } if((rcode = viewparaevga(vmode, 0, 234, &Result)) != NO_ERROR) {
        puts("Error in displaying result");
        return;
    } if((rcode = viewparaevga(vmode, 256, 234, &Oper2)) != NO_ERROR) {
        puts("Error in displaying oper2");
        return;
    }

} pause();            /* Wait for key press */ setvideomode(3);    /* Set text display mode */

}

/* Increase/decrease the brightness of an image
    Demos: changebright()
*/
void Change_Bright(void)
{
    int val, rcode;

/* Get user input, convert to int */
    val = getnum("\nChange brightness:"
                 "\nEnter amount to change brightness: ");
    if(val == -1)    /* -1 => invalid entry */
        return;
    fputs(" Working... ", stdout);
    if((rcode=changebright(val, &Image, &Result)) != NO_ERROR)
        error_handler(rcode);
} void Negate(void)
{ int rcode;

if((rcode=negative(&Image, &Result)) != NO_ERROR)
        error_handler(rcode);

}
void SetWhite(void)
{ int i, j, rcode;

for(i=Image.sty; i<=Image.endy; i++) { for(j=Image.stx; j<=Image.endx; j++) { if((rcode=setpixelgray(&Image, j, i, 254)) != NO_ERROR) {
                printf("\nsetpixel error at %d, %d ", j, i);
                return;
            }

}
    }
} void LoThreshold_Image(void)
{
    int i, j, gray, thresh, rcode;

/* Get user input, convert to int */
    thresh = getnum("\nThreshold:"
                    "\nEnter threshold: ");
    if(thresh < 0 || thresh > 255)   return;
```

```c
      rcode = threshold(thresh, &Image, &Result);
      if(rcode != NO_ERROR)   /* Display any error messages */
         error_handler(rcode);

rcode = subimage(&Image, &Result, &Result);
      if(rcode != NO_ERROR)   /* Display any error messages */
         error_handler(rcode);

/*
      for(i=Image.sty; i<=Image.endy; i++) { for(j=Image.stx; j<=Image.endx; j++) { if((gray=getpixelgray(&Image, j, i)) > thresh)
                  setpixelgray(&Result, j, i, 0);
            else setpixelgray(&Result, j, i, gray);

}
      }
*/

} void Threshold_Image(void)
{
   int i, j, gray, thresh, rcode;

/* Get user input, convert to int */
   thresh = getnum("\nEnter High Threshold: ");
   if(thresh < 0 || thresh > 255)  return;

rcode = threshold(thresh, &Image, &Result);
   if(rcode != NO_ERROR)   /* Display any error messages */
      error_handler(rcode);

rcode = subimage(&Image, &Result, &Result);
   if(rcode != NO_ERROR)   /* Display any error messages */
      error_handler(rcode);

thresh = getnum("\nEnter Low Threshold: ");
   if(thresh < 0 || thresh > 255)  return;

rcode = threshold(thresh, &Result, &Result);
   if(rcode != NO_ERROR)   /* Display any error messages */
      error_handler(rcode);

}

/* Display the histogram of an image on VGA, EGA, CGA, or HGC.
   Demos: calchisto(), showhisto(), setvideomode()
*/
void DispHisto(void)
{
   long his_table[256];    /* Allocate space for population data */
   int vmode, rcode;
   int bar=0, txt=0, bck=15; /* Colors to use for histogram display */

/* Choose a display mode */
   if(Vflags.VGAflag || Vflags.EGAflag)
      vmode = EGA_;
   else if(Vflags.CGAflag)
      vmode = CGA_;
   else if(Vflags.HGCflag)
      vmode = MDA_;
   else {
      error_handler(NO_VIDADAP);   /* No suitable video adapter */
      return;
   }
   /* Calc histogram */
   if((rcode=calchisto(his_table, &Result)) == NO_ERROR) {
      his_table[0] = 0;
      setvideomode(vmode);     /* Set MDA(7), CGA(6), or EGA(16) */
      if(vmode == MDA_ )       /* Set Hercules graphics mode if vmode == 7 */
```

```
        set_hgc_graph(1);
        /* Display the histogram */
        /*if((rcode=showhisto2(vmode, his_table+1, "Histogram", "MRI",
            bar, txt, bck, 1, 255)) == NO_ERROR)
        */ if((rcode=showhisto(vmode, his_table, "Histogram", "MRI",
            bar, txt, bck)) == NO_ERROR)

pause();      /* Wait for key press (defined in VICDEFS.H) */
        }
    if(vmode==MDA_)     /* Disable Herc graphics mode if vmode == 7 */
        set_hgc_graph(0);
    else
        setvideomode(3);     /* Restore video mode */
    if(rcode != NO_ERROR)    /* Display any error messages */
        error_handler(rcode);
}

/* Display image on the PC monitor as an ordered dither in VGA or EGA mode
   Demos: viewdither()
*/
void DitherView(imgdes *image)
{
    int vmode, rcode;
    int scrx=0, scry=0;

if(Vflags.VGAflag)
        vmode = EEGA_;    /* 640x480 16-color mode (0x12) */
    else if(Vflags.EGAflag)
        vmode = EGA_;     /* 640x350 16-color mode (0x10) */
    else {
        error_handler(NO_VIDADAP);   /* No suitable video adapter */
        return;
        }
    setvideomode(vmode);    /* set EGA(0x10) or VGA(0x12) */
    if((rcode=viewdither(vmode, 7, scrx, scry, image)) == NO_ERROR)
        pause();            /* Wait for key press */
    setvideomode(3);        /* Set text mode */
    if(rcode != NO_ERROR)   /* Display any error messages */
        error_handler(rcode);
}

/* Perform any necessary functions before exiting program */
void exitprog(void)
{
    freeimage(&Image);    /* Free any allocated EX/EM/CM */
}

/* Exchange gray levels in an image
   Demos: exchangegray()
*/
void Exchange_Gray(void)
{
    int min, max, val, rcode;

/* Get user input, convert to int */
    min = getnum("\nExchange gray levels:"
                 "\nEnter lower level value to change: ");
    if(min == -1)  return; /* -1 => invalid entry */ max = getnum("\nEnter upper level to change: ");
    if(max == -1)  return;

val = getnum("\nEnter level to change values to: ");
    if(val == -1)  return;
    fputs(" Working... ", stdout);
    rcode = exchangegray(min, max, val, &Image, &Result);
    if(rcode != NO_ERROR)   /* Display any error messages */
        error_handler(rcode);
}

/* Expand contrast of an image
   Demos: expandcontrast()
*/
void Expand_Contrast(void)
{
    int min, max, rcode;
```

```c
   /* Get user input, convert to int */
   min = getnum("\nExpand contrast:"
                "\nEnter lower level for expanding contrast: ");
   if(min == -1)  return;

max = getnum("\nEnter upper level for expanding contrast: ");
   if(max == -1)  return;
   fputs(" Working... ", stdout);
   rcode = expandcontrast(min, max, &Image, &Result);
      if(rcode != NO_ERROR)    /* Display any error messages */
         error_handler(rcode);
}

/* Kodalith
*/ long fluid = 0;

void Kodalith_Image(void)
{
   int min, max, rcode;

/* Get user input, convert to int */
   min = getnum("\nKodalith:"
                "\nEnter threshold: ");
   if(min < 0 || min > 255)  return;

rcode = kodalith(min, &Image, &Result);
   if(rcode != NO_ERROR)    /* Display any error messages */
      error_handler(rcode);

if((rcode = pixelcount(255, 255, &fluid, &Result)) != NO_ERROR) {
      error_handler(rcode);
      return;
   } printf("\nFluid (Kodalith) Pixel Count: %ld\n", fluid);

pause();

}

/* Threshold
*/ void HiThreshold_Image(void)
{
   int thresh, rcode;

/* Get user input, convert to int */
   thresh = getnum("\nThreshold:"
                   "\nEnter threshold: ");
   if(thresh < 0 || thresh > 255)  return;

rcode = threshold(thresh, &Image, &Result);
   if(rcode != NO_ERROR)    /* Display any error messages */
      error_handler(rcode);

}

/* Multiply
*/ void Multiply_Image(void)
{
   int fact, rcode;

/* Get user input, convert to int */
```

```c
    fact = getnum("\nMultiply:"
                "\nEnter factor: ");
    if(fact < 0 || fact > 255)  return;

rcode = multiply(fact, &Image, &Result);
    if(rcode != NO_ERROR)   /* Display any error messages */
        error_handler(rcode);
}

/* Divide
*/ void Divide_Image(void)
{
    int fact, rcode;

/* Get user input, convert to int */ fact = getnum("\nDivide:"
                "\nEnter factor: ");
    if(fact < 0 || fact > 255)  return;

rcode = divide(fact, &Image, &Result);
    if(rcode != NO_ERROR)   /* Display any error messages */
        error_handler(rcode);

}

/* Blur
*/ void Blur_Image(void)
{
    int rcode;

/* Get user input, convert to int */ rcode = blur(&Image, &Result);
    if(rcode != NO_ERROR)   /* Display any error messages */
        error_handler(rcode);

}

/* Pixellize.
*/ void Pixellize_Image(void)
{
    int fact, rcode;

/* Get user input, convert to int */ fact = getnum("\nPixellize:"
                "\nEnter factor (2 to 63): ");
    if(fact < 2 || fact > 63)  return;

rcode = pixellize(fact, &Image, &Result);
    if(rcode != NO_ERROR)   /* Display any error messages */
        error_handler(rcode);
}

/* Gently sharpen image
   Demos: sharpengentle()
*/
void Gentle(void)
{
    int rcode;

fputs(" Working... ", stdout);
    rcode = sharpengentle(&Image, &Result);
    if(rcode != NO_ERROR)   /* Display any error messages */
        error_handler(rcode);
}
```

```c
/* Sharpen image with high pass filter
   Demos: sharpen()
*/
void HipassFilter(void)
{
   int rcode;

fputs(" Working... ", stdout);
   rcode = sharpen(&Image, &Result);
   if(rcode != NO_ERROR)    /* Display any error messages */
      error_handler(rcode);
}

/* Improve image contrast through histogram linearization.
   Demos: histolinearize()
*/
void Linearize(void)
{
   int rcode;

fputs(" Working... ", stdout);
   rcode = histolinearize(&Image, &Result);
   if(rcode != NO_ERROR)    /* Display any error messages */
      error_handler(rcode);
}

/* Allocate expanded/extended/conventional memory for image storage. Returns
   NO_ERROR, BAD_MEM (not enough CM), NO_EMM, EMM_ERR, NO_XMM, or XMM_ERR.
   Demos: cmallocimage(), emallocimage(), and xmallocimage()
*/
int mem_alloc(imgdes *image, int iwidth, int ilength)
{
   int rcode;

/* Our strategy is to try to allocate the buffer in EM first,
      then in XM, and finally in CM.
   */
   if((rcode=emallocimage(image, iwidth, ilength)) != NO_ERROR) {
      if((rcode=xmallocimage(image, iwidth, ilength)) != NO_ERROR)
         rcode = cmallocimage(image, iwidth, ilength);
      }
#if VERBOSE == 1
   if(image->ibuff)
      printf("\nCM address allocated: %lx", image->ibuff);
   else if(image->ehandle)
      printf("\nEM handle allocated: %u", image->ehandle);
   else if(image->xhandle)
      printf("\nXM handle allocated: %u", image->xhandle);
   timeout(400);
#endif
    return(rcode);
}

/* Load binary image file (BIF) into Image. BIF image is assumed to have
   an image width of ImgWidth, since there's no header info to tell us
   otherwise.
   Demos: loadbif()
*/
void ReadBif(void)
{
   int length, width, fhr, rcode;
   long filelength(int);
   char fname[80];

fputs("\nEnter filename of binary image file to load: ",stdout);
   gets(Txtbuf);
   if(sscanf(Txtbuf, "%s", fname) < 1)
      return;
   /* Make sure file exists and get its length */
   if((fhr=open(fname, O_BINARY|O_RDONLY)) < 3)
      rcode = BAD_OPN;
   else {
      /* File opened, set image width, calc image length */
      width  = ImgWidth;
      length = (int)(filelength(fhr) / width);
      close(fhr);
```

```c
        /* Resize the image buffer to the file dimensions */
        rcode = resiz_imgbuf(&Image, width, length);
        if(rcode != NO_ERROR)
            printf("\nNot enough memory to load entire image."
                    "\nImage is: %d x %d, Buffer is: %d x %d",
                    width, length, Image.iwidth, Image.ilength);
        printf("\nReading binary file %s...", fname);
        rcode = loadbif(fname, &Image);
        }
    if(rcode != NO_ERROR)   /* Display any error messages */
        error_handler(rcode, fname);
}

/* Resize an image to double size
   Demos: resize(), viewhalftone(), viewvga()
*/ void ResizeImage2(void)
{
    /* Coords of image section to resize */ int rcode, xs=0, ys=0, xe=2*Result.endx, ye=2*Result.endy;

/* Resize image and store at upper left */

/*   copyimgdes(&Result, &desimg);

printf("\nxe = %d, ye = %d", xe, ye);
*/ setvgapalette(desimg.palette);

setimagearea(&desimg, xs, ys, xe, ye);
    if(checkrange_(&desimg) != NO_ERROR)
        puts("\nRange error, desimg");

/*   mouse_show_crsr();
  */
    if((rcode=resize(&Result, &desimg)) == NO_ERROR)
        VgaViewImage(&desimg, 0, 0);

else if(rcode != NO_ERROR)   { /* Display any error messages */
        puts("Resize error: \n");
        error_handler(rcode);
    } pause();
/*   mouse_hide_crsr();
  */
    setvideomode(3);

} void Trace_It(void)
{
    int avg_lvl, rcode;

fputs(" Working... ", stdout);
    /* Calc average level of image */
    avg_lvl = calcavglevel(&Image);
    /* Check that avg_lvl is not an error code */
    if(0 < avg_lvl || avg_lvl < 255) {
        if((rcode=kodalith(avg_lvl, &Image, &Result)) == NO_ERROR)
            rcode = outline(&Image, &Result);
        }
    else
        rcode = avg_lvl;    /* Calcavglevel() returned an error code */
    if(rcode != NO_ERROR)   /* Display any error messages */
        error_handler(rcode);
}

/* 640 x 480 256-color video modes for Tseng, ATI, Paradise, Trident,
   Headland (Vega), and VESA compatible super VGA display adapters.
*/
```

```
#define  TS640X480    0x2e
#define  ATI640X480   0x62
#define  PARA640X480  0x5f
#define  VEGA640X480  0x67
#define  TRID640X480  0x5d
define  VESA640X480  0x101 typedef struct {      /* Super VGA mode/function struct */
    int mode;         /* Video mode to set */
    int (*fctn)(int,int,int,imgdes *);   /* View fctn to use */
    } viewfunct;

/* Display image on PC monitor as super VGA or VGA 320x200 image
   Demos: viewtsengevga(), viewatievga(), viewparaevga(), viewvegaevga(),
   viewtridevga(), viewvesaevga(), setvgapalette(), and viewvga().
*/
void VgaViewImage(imgdes *image, int scrx, int scry)
{
    int rcode, vmode, j, strnum;
    static viewfunct viewlist[] = {
        VESA640X480, viewvesaevga,  /* EVGAflag = 0 => use VESA view fctn */
        TS640X480,   viewtsengevga, /* EVGAflag = 1 => use view Tseng */
        ATI640X480,  viewatievga,
        PARA640X480, viewparaevga,
        VEGA640X480, viewvegaevga,
        TRID640X480, viewtridevga,
        TS640X480,   viewtsengevga,
        };
    int (*viewfct)(int,int,int,imgdes *);
    int (*modefct)(int);
    static char *adapt_str[] = {
        "VESA 640x480x256",    /* VESA: 0x101 */
        "Tseng 640x480x256",   /* Tseng: 0x2e */
        "ATI 640x480x256",     /* ATI: 0x63 */
        "Para 640x480x256",    /* Paradise: 0x5f */
        "Vega 640x480x256",    /* Vega: 0x67 */
        "Trident 640x480x256", /* Trident: 0x5d */
        "Tseng4 640x480x256",  /* Tseng: 0x2e */
        "VGA 320x200x256",     /* VGA 320x200 256-color mode */
        };

/* Check that a VGA adapter is installed */
    if(Vflags.VGAflag == 0) {
        error_handler(NO_VIDADAP);   /* No suitable video adapter */
        return;
    }
    /* If there's no palette data available, create a gray scale palette */
    if(image->palsize == 0) {
        pflag = !pflag;
        make_palette(&image->palette[0]);
        /*
        for(j=0; j<3*256; j++)
            image->palette[j] = (UCHAR)(j / 3);
        */
    }

/* Select view function to use */
    viewfct = viewlist[Vflags.EVGAflag].fctn;
    /* Select video mode to use */
    vmode = viewlist[Vflags.EVGAflag].mode;
    /* Assume mode set routine will be setvideomode() */
    modefct = setvideomode;
    /* Select string number to display text on screen */
    strnum = Vflags.EVGAflag;
    /* Use a super VGA mode and a specific view function if possible */
    if(inrange(TSENG, Vflags.EVGAflag, TSENG4)) {
        /* Select video mode set function (Vega requires special treatment) */
        if(Vflags.EVGAflag == VEGA)
            modefct = setvegavmode;
    }
    /* Otherwise, use a VESA super VGA or standard VGA view function */
    else {
        /* Test for VESA driver and vmode support */
        if(vesamodeinfo(vmode) == NO_ERROR)
            /* VESA mode supported: use VESA video mode set function */
            modefct = setvesamode;
        else {              /* Super VGA display not possible, */
            vmode = VGA_;   /* use 320 x 200 256-color VGA mode */
            strnum = 7;     /* Display VGA string */
```

```
            }
        }
/*
    printf("\nvmode = %d", vmode);
    pause();
*/
    modefct(vmode);            /* Set the video display mode */
    setvgapalette(image->palette);  /* Set the VGA palette */
    if(vmode == VGA_)                      /* Based on video mode, */
        rcode = viewvga(scrx, scry, image); /* use standard VGA view fctn */
    else
        rcode = viewfct(vmode, scrx, scry, image); /* or super VGA view fctn */

/*  if(rcode == NO_ERROR) {
        crt_src(22, 5);
        bprint(220, "Vmode = %s mode", adapt_str[strnum]);
    }
*/ if(rcode != NO_ERROR)  /* Display any error messages */
        error_handler(rcode);

}

/* Vega video mode set requires special treatment.
   Or, setvideomode() can be used with non-standard mode numbers.
   Standard modes:   0x66, 0x67, 0x68, 0x69
   Equivalent modes: 0x1a, 0x1b, 0x1c, 0x1d
*/
int setvegavmode(int vmode)
{
    regs.x.ax = 0x06f05;        /* Extended mode set */
    regs.h.bl = (UCHAR)vmode;   /* vmode = mode number */
    int86(0x10, ®s, ®s);
    return(NO_ERROR);
}

/* Write image to disk as a binary image file
   Demos: savebif()
*/
void WriteBif(void)
{
    int rcode;
    char fname[80];

fputs("\nEnter filename of image to save as a binary file: ",stdout);
    gets(Txtbuf);
    if(sscanf(Txtbuf,"%s",fname) < 1)
        return;
    printf("\nWriting %s as binary file...", fname);
    rcode = savebif(fname, &Image);
    if(rcode != NO_ERROR)   /* Display any error messages */
        error_handler(rcode, fname);
}

/* Use BIOS function to display text
*/
void bprint(int attr, char *string, ...)
{
    va_list arg_ptr;
    char buff[82];      /* Handle up to 80 chars */ va_start(arg_ptr, string);   /* "arg_ptr" points to format string */
    vsprintf(buff, string, arg_ptr);
    va_end(arg_ptr);

/* Use BIOS function to display up to 80 chars of text */
    bios_write(attr, buff);
}

/* Use BIOS function to display up to 80 chars of text */
void bios_write(int attr, char *buff)
{
```

```c
    int j;
    regs.h.bl = (UCHAR)attr;        /* Display intensity */
    for(j=0; j<80 && buff[j]; j++) {
        regs.x.ax = buff[j] | (0x0e<<8);
        int86(0x10, ®s, ®s);  /* Use video int fctn = 14 */
        }
}

/* Clear the PC monitor
*/
void crt_cls(void)
{
    crt_src(0, 0);
    regs.x.ax = 0x0600;
    regs.h.bh = 7;
    regs.x.cx = 0;
    regs.x.dx = 0x184f;
    int86(0x10, ®s, ®s);      /* Use video int fctn = 6 */
}

/* Get row, col position
*/
void crt_grc(int *col, int *row)
{
    regs.h.ah = 3;
    regs.h.bh = 0;                  /* page=0 */
    int86(0x10, ®s, ®s);      /* Use video int fctn = 6 */
    *row = regs.h.dh; *col = regs.h.dl;
}

/* Set row, col position
*/
void crt_src(int row, int col)
{
    regs.x.ax = 0x0200;
    regs.h.dh = (UCHAR)row;
    regs.h.dl = (UCHAR)col;
    regs.h.bh = 0;                  /* Page=0 */
    int86(0x10, ®s, ®s);      /* Use video int fctn = 6 */
}

/* Turn cursor ON/OFF
*/
void cursor(int mode)
{
    regs.x.ax = 0x0100;
    regs.x.cx = (mode) ? 0x0607 : 0x2000;  /* CX controls cursor size */
    int86(0x10, ®s, ®s);      /* Use video int fctn = 1 */
}

/* Erase to end of line
*/
void erase_eol(void)
{
    int col, row;

crt_grc(&col, &row);            /* get (col,row) position */
    crt_src(row, col=0);            /* move to (0,row) position */
    regs.x.ax = 0x0600;             /* erase window fctn */
    regs.x.cx = col | (row<<8);     /* CH = row, CL = col */
    regs.x.dx = 79  | (row<<8);     /* DH = row, DL = col = 79 */
    regs.h.bh = 7;                  /* Attribute = 7 */
    int86(0x10, ®s, ®s);      /* Use video int fctn = 6 */
}

/* Use BIOS function to display error messages
*/
void errmsg(char *fmt, ...)
{
    va_list arg_ptr;
    char buff[82];       /* Handle up to 80 chars */ va_start(arg_ptr, fmt); /* "arg_ptr" points to format string */
    vsprintf(buff, fmt, arg_ptr);
    va_end(arg_ptr);
    chirp();
    bios_write(255, buff);  /* Use color 255 */
    bios_write(255, " Press any key to continue ");
    pause();
}
```

```c
/* Return a pointer to an error message representing errcode.
   If errcode = NO_ERROR, return NULL.
*/
char *error_list(int errcode)
{
    switch(errcode) {
        case NO_ERROR:
            return(NULL);
        case BAD_RANGE:
            return("\n\r** Value(s) out of range **");
        case BAD_DSK:
            return("\n\r** Disk full, %s not written **");
        case BAD_OPN:
            return("\n\r** Cannot open %s **");
        case BAD_FAC:
            return("\n\r** Invalid Data **");
        case BAD_TIFF:
        case BAD_IFD:
        case BAD_BPS:
        case BAD_CMP:
            return("\n\r** Unreadable TIF format: %s **");
        case BAD_CRT:
            return("\n\r** Cannot create %s **");
        case BAD_FTPE:
            return("\n\r** Invalid filetype **");
        case VMODE_ERR:
            return("\n\r** Invalid video mode **");
        case BAD_MEM:
            return("\n\r** Insufficient memory **");
        case BAD_PIW:
            return("\n\r** Unreadable PIW format: %s **");
        case BAD_PCX:
            return("\n\r** Unreadable PCX format: %s **");
        case BAD_GIF:
            return("\n\r** Unreadable GIF format: %s **");
        case NO_EMM:
            return("\n\r** Expanded memory manager not found **");
        case EMM_ERR:
            return("\n\r** Expanded memory manager error:");
        case SCAN_ERR:
            return("\n\r** Scanner error **");
        case NO_XMM:
            return("\n\r** Extended memory manager not found **");
        case XMM_ERR:
            return("\n\r** Extended memory manager error:");
        case CM_ERR:
            return("\n\r** CM handle overflow error **");
        case PRT_ERR:
            return("\n\r** Printer error **");
        case TIMEOUT:
        case NO_DATA:
        case COM_ERR:
        case NO_DIG:
            return("\n\r** Error in receiving image **");
        case NO_VIDADAP:
            return("\n\r** No suitable video adapter found for display **");
        default:
            return("\n\r** Error encountered **");
    }
}

/* Error handler for various functions. If error_list returns a vaild
   address, display an error message. Errors are listed in VICERROR.H.
*/
void error_handler(int errcode, ...)
{
    va_list arg_ptr;
    char *errstr, *sptr, buff[128];      /* Handle up to 128 chars */ if((errstr=error_list(errcode)) != NULL) {
        chirp();
        while(kbhit()) getkey();    /* Flush the keyboard buffer */
        va_start(arg_ptr, errcode);
        vsprintf(buff, errstr, arg_ptr);
        va_end(arg_ptr);
        /* Add EM/XM errcode */
        if(errcode == EMM_ERR || errcode == XMM_ERR) {
            sptr = strchr(buff, '\0'); /* Find end of string */
            sprintf(sptr, " %x **", (errcode==EMM_ERR) ? emerror() : xmerror());
        }
```

```c
        bios_write(240, buff);    /* Use color 240 */
        bios_write(240, " Press any key to continue ");
        pause();
        }
}

/* Get user input and return value or -1 for invalid entry
*/
int getnum(char *prompt)
{
    char buff[80];
    int tempint;

fputs(prompt, stdout);
    gets(buff);
    if(sscanf(buff, "%d", &tempint)<1)
        return(-1);        /* -1 => invalid entry */
    return(tempint);
}

/* Enable/disable Hercules graphics mode
*/
void set_hgc_graph(int mode)
{
#define  IndexReg    0x3b4
#define  ModeReg     0x3b8
#define  StatusReg   0x3ba
define  ConfigReg   0x3bf char far *addr = (char far *)0xb0000000L;
    static UCHAR GraphVals[]= {0x35,0x2d,0x2e,0x7,0x5b,2,0x57,0x57,2,3,0,0};
/*  static UCHAR TextVals[] = {
    0x61,0x50,0x52,0xf,0x19,6,0x19,0x19,2,0xd,0xb,0xc};
*/
    unsigned j;

if(mode) {         /* Enable Hercules graphics mode */
        outp(ConfigReg, 3);      /* Allow both graphics pages */
        outp(ModeReg, 2);        /* Blank the screen */
        for(j=0; j<12; j++) {
            outp(IndexReg, j);              /* Reg to write */
            outp(IndexReg+1, GraphVals[j]);  /* Data reg */
            }
        for(j=0; j<0x8000; j++)    /* Clear HGC screen */
            *addr++ = 0;
        outp(ModeReg, 0x0a);      /* Turn on the screen */
        }
    else {          /* Set Hercules text mode */
        outp(ConfigReg, 0);   /* Disable graphics mode */
        outp(ModeReg, 0);     /* Blank the screen */
        for(j=0; j<12; j++) {
            outp(IndexReg, j);              /* Reg to write */
            outp(IndexReg+1, GraphVals[j]);  /* Data reg */
            }
        outp(ModeReg, 0x28);     /* Enable blink, turn on screen */
        }
} define MAXDIM 10
/* Resize the image buffer. Returns NO_ERROR if successful or BAD_MEM if
   new allocation failed. Does not allow image buffer widths < MAXDIM
   or image buffer lengths < MAXDIM.
*/
int resiz_imgbuf(imgdes *image, int width, int length)
{
    int rcode;

/* Release the current image buffer */
    freeimage(image);
    /* Try to allocate the new image buffer, but don't allow
       width < ImgWidth or length < ImgLength
    */
    if(width < MAXDIM)
        width = MAXDIM;
    if(length < MAXDIM)
        length = MAXDIM;
    rcode = mem_alloc(image, width, length);
    if(rcode != NO_ERROR) {
        /* Didn't get what we asked for, reallocate initial buffer */
```

```c
            mem_alloc(image, ImgWidth, ImgLength);  /* Assume we get it */
            rcode = BAD_MEM;
            }
      return(rcode);
} extern void * _cdecl strcpyn_(void huge *,void huge *,unsigned);
/*extern void _cdecl writCGA_(int,int,int,char *);
*/
/* 6 routines are in egahisto.asm */
extern void _cdecl EGAhisto_(UCHAR *,int,int);
extern void _cdecl CGAhisto_(UCHAR *,int,int);
extern void _cdecl HGChisto_(UCHAR *,int,int);
extern void _cdecl writEGA_(int,int,int,char *);
extern void _cdecl writHGC_(int,int,int,char *);

extern void _cdecl set_ega_window_(int,int,int,int,int);

extern void _cdecl crt_src_(int,int);

/* Produce framed histo on HGC/CGA/EGA/VGA
      TitleStr and LegendStr are centered.  Color values bar_col,txt_col,
      and bck_col apply to EGA and VGA only. Valid vmodes are 6 (CGA),
      7 (HGC), 16 (EGA), and 18 (EEGA). Returns NO_ERROR, BAD_RANGE
      (No pixels!), or VMODE_ERR (invalid video mode).
*/
int _cdecl showhisto2(int vmode, long *his_table, char *titlestr,
      char *legendstr, int bar_col, int txt_col, int bck_col, int st, int no)
{
      void (_cdecl *showfct)(UCHAR *,int,int);
      void (_cdecl *writstr)(int,int,int,char *);
      char sstr[80];
      UCHAR tab[260];
      int sp, flag=0;
      long *lp;
      long maxpop;
      static char *dotstr = ".  .   .   .   .   .   .   .   .   .   .   .   .";
      static char *numstr = "0   20   40   60   80  100 120 140 160 180 200 220 240";
      int titlerow=0, axisrow=20, legendrow=23;

for(sp=0; sp<260; sp++) tab[sp] = 0;

if(vmode==EEGA_ || vmode==EGA_) {
                  showfct = EGAhisto_;
                  writstr = writEGA_;
                  }
/*    else if(vmode == CGA_) {
                  showfct = CGAhisto_;
                  writstr = writCGA_;
                  }
*/    else if(vmode == MDA_) {
                  showfct = HGChisto_;
                  writstr = writHGC_;
                  }
      else
                  return(VMODE_ERR);            /* Invalid video mode */

/* Find most populated bin = maxpop */
      lp = his_table;
      maxpop = *lp++;          /* Initialize maxpop and point lp at bin 1*/
      sp = 255 - st;
      while(sp--) {                    /* Do next 255 bins */
            if(maxpop < *lp)
                  maxpop = *lp;
            lp++;
            }
      if(maxpop == 0)
            return(BAD_RANGE);               /* No pixels! */
/* Normalize to population = 128 if maxpop >= 128 */
      lp = his_table;
      if(maxpop >= 128) {
            flag = 1;
            maxpop >>= 7;
            }
      for(sp=0; sp<no; sp++) {
            /* val = bin/(maxpop/128) or bin*128/maxpop */
```

```c
            tab[sp] = (UCHAR)((flag ? (*lp) : (*lp * 128)) / maxpop);
            lp++;
            }
/* Write title str */
strcpyn_(sstr, titlestr, 74);
sp = 40 - (strlen(sstr) / 2);

if(vmode >= EGA_)           /* Set fore col for a window, move cursor */
                set_ega_window_(0, 0, 79, 349, bck_col);
        writstr(titlerow, sp, txt_col, sstr);

writstr(axisrow, 8, txt_col, dotstr);
        writstr(axisrow+1, 8, txt_col, numstr);
        /* For writ EGA, mul row by 14 and col by 8 */

/* Write legend str */
        strcpyn_(sstr, legendstr, 74);
        sp = 40 - (strlen(sstr) / 2);
        writstr(legendrow, sp, txt_col, sstr);
        showfct(tab, bar_col, 0);
        return(NO_ERROR);
}

/* floodfill */

/*  floodfill is a modified version of the PAINT routine
            which is the fill routine for complex areas.
         */ typedef struct {
                UINT x, y;
            } UCOOR;

typedef struct {
                UCOOR pt;
                UINT *x_stack, *y_stack;
                /*UTINY *pattern;
                INT   n_slices;
                UINT  bcolor, fillcolor; */
                UINT  count;
            } fill;

fill _paint;

UINT stack_size = 500;

UINT floodfill(imgdes *src, imgdes *dst, UINT x, UINT y)
{
UINT *x_mem_base, *y_mem_base;
UINT paint_line();

_paint.pt.x = x;
_paint.pt.y = y;

x_mem_base = _paint.x_stack = (UINT *)malloc(stack_size * sizeof(UINT));
y_mem_base = _paint.y_stack = (UINT *)malloc(stack_size * sizeof(UINT));

_paint.count = 0;

/* check for possible error conditions
                 */
if (!x_mem_base OR !y_mem_base) {
     free(x_mem_base);
     free(y_mem_base);
        printf("\n\7NOT ENOUGH STACK SPACE\n");
        return -1;
}
                /* paint it! */ while ((paint_line(src, dst) > 0) AND (_paint.count < stack_size));
```

```
free(x_mem_base);
free(y_mem_base);

return(_paint.count);
/*
return ((_paint.count >= stack_size) AND (_paint.count != 0xFFFF))
    ? -1 : SUCCESS;
*/

}

/*   _paintline() is called by PAINT() to paint a line, and then
             *   check the lines above and below it to see if they should be
             *   written out at a later time.
             */

UINT paint_line(imgdes *src, imgdes *dst)
{
UINT lower_y, pt_x;
UINT pixcolor, l_bnd, r_bnd, r_limit, match_type;

long len;

/* find left and right points of line to draw, and draw it! */ r_bnd = rightborder(src, _paint.pt.x, _paint.pt.y);
l_bnd = leftborder(src, _paint.pt.x, _paint.pt.y);
if (l_bnd == -1) then l_bnd = 0;
if ((len = (long)(r_bnd - l_bnd + 1)) > 0) {
    total += len;

fill_image_line(dst, l_bnd, _paint.pt.y, r_bnd, 255);
}
else return _paint.count;

/*   this routine executes twice--
             * checking the lines above and below the current line, to determine
             * if those lines should be drawn at some later time.  If so, it will
             * put the coordinate onto the x and y stacks.
             */ r_limit = r_bnd;

for (lower_y = _paint.pt.y - 1; lower_y < _paint.pt.y + 2; lower_y += 2){
    pt_x = l_bnd;     /* Start on previous left boundary */

/* Loop unless the row is outside screen boundaries */ if (inrange(0, lower_y, 255)) { do {
            pixcolor = getpixelgray(src, pt_x, lower_y);
            if (pixcolor == 0)
                match_type = NO;
            else {
                match_type = YES;
                if ((pixcolor != 255)) {
                    if(_paint.count < stack_size) {
                        *(++_paint.x_stack) = pt_x;
                        *(++_paint.y_stack) = lower_y;
                        _paint.count++;
                    }
                    else {
                        printf("\n\7count = %u, stack = %u ", _paint.count,
                            stack_size);

return stack_size;
                    }

}

} pt_x = find_pel(src, pt_x, lower_y, 0, 256, match_type);

} while (inrange(1, pt_x, r_limit));
```

```
                }
        }
_paint.pt.x = *_paint.x_stack--;   /* pop coordinate from stack for the next call */
_paint.pt.y = *_paint.y_stack--;

return _paint.count--;             /* decrement the count */

}

UINT out_color(UINT lo, UINT x, UINT hi)
{
   if((x <= lo) || (x >= hi)) return 1;
   else return 0;

}

/* routines local to floodfill */

UINT leftborder (imgdes *im, UINT x, UINT y)
{
        UINT pixel;

do {
                --x;
                pixel = getpixelgray(im, x, y);
                if(!pixel) break;
        } while (x > 0) ;
        return x+1;
}

UINT rightborder (imgdes *im, UINT x, UINT y)
{
        UINT pixel;

do {
                ++x;
                pixel = getpixelgray(im, x, y);
                if(!pixel) break;
        } while (x < 256) ;
        return x-1;
}

UINT find_pel(imgdes *im, UINT x, UINT y, UINT lo_color,
        UINT hi_color, UINT match_type)
{
    register UINT i;

if(match_type == YES) { for(i=x; i<256; i++)
           if(out_color(lo_color, getpixelgray(im, i, y), hi_color))
               return i;
    } else for(i=x; i<256; i++)
           if(!out_color(lo_color, getpixelgray(im, i, y), hi_color))
               return i;

return 256;

} void fill_image_line(imgdes *im, UINT xl, UINT y, UINT xr, UINT color)
{ register UINT i;

for(i=xl; i<=xr; i++)
          setpixelgray(im, i, y, color);

}
```

```c
UCHAR **calloc_2d_uc(int rows, int cols)
{

/* dynamically allocate and zero a 2d, long array on the near heap */ register int i, j;

UCHAR **m;

m = (UCHAR **)malloc(rows * sizeof(UCHAR *));
    if(!m) return(NULL);

for(i=0; i<rows; i++) {
        m[i] = (UCHAR *)malloc(cols);
        if(!m[i]) return(NULL);
    } return(m);

}
void Make_Big(void)
{ int i, j, x, y, lowy = 240;

zeroimage(0, &desimg);

/* copy top 2 images to top half of desimg */ for(y=j=0; j<lowy; j++, y++) { for(x=i=0; i<ImgLength; i++, x++)
            setpixelgray(&desimg, x, y, getpixelgray(&Image, i, j));

for(i=0; i<ImgLength; i++, x++)
            setpixelgray(&desimg, x, y, getpixelgray(&Oper, i, j));

}

/* copy bottom 2 images to bottom half of desimg */ for(j=0; j<lowy; j++, y++) { for(x=i=0; i<ImgLength; i++, x++)
            setpixelgray(&desimg, x, y, getpixelgray(&Result, i, j));

for(i=0; i<ImgLength; i++, x++)
            setpixelgray(&desimg, x, y, getpixelgray(&Oper2, i, j));

} setvgapalette(desimg.palette);

VgaViewImage(&desimg, 0, 0);

pause();
       setvideomode(3);

}

/* Write image to disk as a tif image file
*/ void WriteTif(void)
{
    int rcode;
    char fname[80];

fputs("\nEnter filename of image to save as a TIF file: ",stdout);
    gets(Txtbuf);
    if(sscanf(Txtbuf,"%s",fname) < 1)
        return;
    printf("\nWriting %s as TIF file...", fname);
```

```
    ResizeImage2();

rcode = savetif(fname, &desimg, 0);   /* no compression */
    if(rcode != NO_ERROR)    /* Display any error messages */
       error_handler(rcode, fname);
}

/* Load TIF into Image. TIF image is assumed to have
   an image width of 2*ImgWidth,
*/ void ReadTif(void)
{
    int length, width, fhr, rcode;
    long filelength(int);
    char fname[80];

zeroimage(0, &desimg);

fputs("\nEnter filename of TIF image file to load: ",stdout);
    gets(Txtbuf);
    if(sscanf(Txtbuf, "%s", fname) < 1)
       return;
    /* Make sure file exists and get its length */
    if((fhr=open(fname, O_BINARY|O_RDONLY)) < 3)
       rcode = BAD_OPN;
    else {
       printf("\nReading TIF file %s...", fname);
       rcode = loadtif(fname, &desimg);
       }
    if(rcode != NO_ERROR)    /* Display any error messages */
       error_handler(rcode, fname);

setvgapalette(desimg.palette);

VgaViewImage(&desimg, 0, 0);

pause();
    setvideomode(3);

}

/* Fuzzy modification of c-means alg. via J. Keller
   6/3/92
*/ void fuzzprob(imgdes *src1_image, imgdes *src2_image, imgdes *mask_image,
              double m, int nc, int pix, UCHAR *x, UCHAR *y, UCHAR **mem)
{
    int i, j, k, l, csf, gry, wht = 0, rcode, fl, iter, itflag, val, ind;
    int pix0, pix1, pix2;

UCHAR u[2], max;
    UINT **d2;

long pcount;

double ps, xx, yy, zz, cc2[NC][2], cc0[NC][2], mn[NC],
           num0, num1, mu, a, b, den, e, f, g,
           ee, nu[NC], dd, mm, sum, d, m2;

double eps = 0.1;
    double pow(), fabs();

FILE *fp, *fopen();

/*
    if((d2 = calloc_2d_uint(nc, pix)) == 0) {
       puts("\nNot enough mem for d2\n");
       pause();
       return;
    }
 */
```

```
    if((rcode = pixelcount(255, 255, &pcount, mask_image)) != NO_ERROR) {
       error_handler(rcode);
       return;
} printf("\nBrain Pixel Area: %ld\n", pcount);

if(m <= 1.0) m = 2.0;
else mm = 1.0/(m - 1.0);

fp = fopen("gray", "w");
fprintf(fp, "%d\n", pix);

iter = 0;

xx = (double)pix;
yy = (double)pcount;

/* store cluster centroids */ for(j=0; j<nc; j++) {
    cc2[j][0] = cc1[j][0];      /* T1 image */
    cc2[j][1] = cc1[j][1];      /* T2 image */
}

/* iteration loop */ printf("\nComputing iteration:");

do { iter++;

printf(" %2d:", iter);

/* reassign cluster centers */ for(j=0; j<nc; j++) {
        cc0[j][0] = cc1[j][0];
        cc0[j][1] = cc1[j][1];
    }
/* compute nu[i]  */
  for(j=0; j<nc; j++) { a=b=num0 = den = 0.0;

for(i=0; i<pix; i++) { d = (double)x[i] - cc0[j][0];
          e = (double)y[i] - cc0[j][1];
          f = (d * d) + (e * e);
          g = (double)mem[j][i]/100.0;
          ee = pow(g, m);
          num0 += (ee * f);
          den  += ee;

} nu[j] = num0/den;
      printf("\nNu[%d] = %f", j, nu[j]);

}

/* compute memberships, update prototypes */ sum = 0.0;
```

```
    for(j=0; j<nc; j++) { a = b = num0 = num1 = den = 0.0;
        mn[j] = 0.0;

for(i=0; i<pix; i++) { d = (double)x[i] - cc0[j][0];
            e = (double)y[i] - cc0[j][1];
            f = (d * d) + (e * e);
            ee = pow((f/nu[j]), mm);

mu = 1.0/(1.0 + ee);

mem[j][i] = (UCHAR)(100.0 * (mu + 0.005));

mn[j] += mu;
        ee = pow(mu, m);
        den += ee;
        a += (ee * (double)x[i]);
        b += (ee * (double)y[i]);

}

/* update prototypes */

/*      mn[j] /= xx;
 */
        sum += mn[j];

cc1[j][0] = a/den;    cc1[j][1] = b/den;
        printf(" proto[%d] = %.1f, ", j, cc1[j][1]);
        printf(" %.4f ", mu);

} for(j=0; j<nc; j++) {
        mn[j] /= sum;
        printf("\nMem[%d] = %f", j, mn[j]);
    }

/* check difference in cluster centers from previous iteration */ for(itflag = j = 0; j<nc; j++) {
        num0 = fabs(cc1[j][0] - cc0[j][0]) + fabs(cc1[j][1] - cc0[j][1]);
        printf(" Diff: %6.3f ", num0);
        if(num0 > eps)
            {itflag = 1; break;}
    }

/*      printf("\nitflag = %d", itflag);
*/

}
    while(itflag);

printf("\n\nClustering complete ... ");

/*
    for(j=0; j<nc; j++)
        printf("\nOverall cluster center %d difference = %.2f ",
            j+1, cc2[j] - cc1[j]);
*/ printf("\n");

if(fluid != 0) {
        zz = (double)fluid;    /* fluid area measured by thresholding (kodalith) */
        yy = xx + zz;          /* total area used */ for(j=0; j<nc; j++) {
            ps = 100.0 * ((xx * mn[j])/yy);
            printf("\nPercentage of cluster %d = %5.1f, Center value = %3.0f ",
                j+1, ps, cc1[j][1]);
        }
```

```
        ps = 100.0  *  (zz/yy);
        printf("\nPercentage of fluid cluster %d = %5.1f ", j+1, ps);
    }
    else {
        for(j=0; j<nc; j++) {
            ps = 100.0 * mn[j];
            printf("\nPercentage of cluster %d = %5.1f, Center value = %3.0f ",
                j+1, ps, ccl[j][1]);
        }
    }
    fluid = 0;

printf("\n\n");

/*
    if(nc == 2) ccl[2] = 0.0;
*/
    zeroimage(0, &Result);

/* defuzzify and create result image */ k = j = 0;

do { i = 0;

do {

/* use T2 image centroids as a basis */ if(getpixelgray(mask_image, i, j)) {
                    pix1 = getpixelgray(src1_image, i, j);
                    pix2 = getpixelgray(src2_image, i, j);
                    if(pix1 && pix2) {
                        csf = (int)((ccl[0][1] * (double)mem[0][k])/100.0);
                        gry = (int)((ccl[1][1] * (double)mem[1][k])/100.0);
                        if(nc == 3)
                            wht = (int)((ccl[2][1] * (double)mem[2][k])/100.0);

val = csf + gry + wht;
                        setpixelgray(&Result, i, j, val);
                        k++;

/*
            fprintf(fp, "%d %d %d\n", pix1, pix2, val);
            */ fprintf(fp, "%d %d %d\n", mem[0][k], mem[1][k], mem[2][k]);

}
                } i++;

}
        while(i < 256);

j++;

}
    while(j < 256);

fclose(fp);
    pause();

}

UINT gethist(imgdes *src1_image, imgdes *src2_image, imgdes *mask_image,
            UCHAR *x, UCHAR *y)
{ int i, j;
    UINT k;
```

```
    int pix0, pix1, pix2;

/* fill buffer */ k = j = 0;

do { i = 0;

do { pix0 = getpixelgray(mask_image, i, j);
              pix1 = getpixelgray(src1_image, i, j);
              pix2 = getpixelgray(src2_image, i, j);

if(pix0) {
                if(pix1 && pix2) {
                    x[k] = pix1;
                    y[k] = pix2;
                  k++;
              }
           } i++;

}
       while(i < 256);

j++;

}
    while(j < 256);

printf("\nNumber of pixels used = %d\n", k);

return(k);

} static double msq[101];

void mem_sqr(void)
{ int i;
  double x, y;

y = 4.0/3.0;

for(i=0; i<101; i++) {
       x = (double)i;
/*     msq[i] = (x * 0.01) * (x * 0.01);
*/
       msq[i] = pow((x * 0.01), y);

}
} void fuzzcmns(imgdes *src1_image, imgdes *src2_image, imgdes *mask_image,
          double m, int nc, int pix, UCHAR *x, UCHAR *y, UCHAR **mem)
{ int i, j, k, l, ii, csf, gry, wht = 0, rcode, fl, iter, itflag, val, ind;
    int pix0, pix1, pix2;

UCHAR u[2], max;

long pcount;

double ps, xx, yy, zz, cc2[NC][2], cc0[NC][2], mn[NC], mu[NC], num[NC][2],
           den[NC], d2[NC], e, dd, mm, sum, d, m2;

double eps = 0.1, f;
```

```
    double pow(), fabs();

FILE *fp, *fopen();

if(m <= 1.0) m = 2.0;
    else mm = 1.0/(m - 1.0);

mem_sqr();
/*
    printf("\nm = %.1f, mm = %.1f\n", m, mm);
    pause();
*/ mu[2] = 0.0;

if((rcode = pixelcount(255, 255, &pcount, mask_image)) != NO_ERROR) {
        error_handler(rcode);
        return;
    }

/*  printf("\nBrain Pixel Area: %d\n", pcount);
*/ fp = fopen("gray", "w");
    fprintf(fp, "%d\n", pix);

iter = 0;

xx = (double)pix;
    yy = (double)pcount;

/* store original cluster centers */ for(j=0; j<nc; j++) {
        cc2[j][0] = cc1[j][0];    /* T1 image */
        cc2[j][1] = cc1[j][1];    /* T2 image */
    }

/* iteration loop */
/*
    printf("\nITER     CC1      CC2      CC3");
    printf("\n---------------------------------");
*/ printf("\nComputing iteration:");

do { iter++;

printf(" %2d", iter);

/* reassign cluster centers */ for(j=0; j<nc; j++) {
            cc0[j][0] = cc1[j][0];
            cc0[j][1] = cc1[j][1];
            mn[j] = 0.0;
            num[j][0] = den[j] = 0.0;
            num[j][1] = 0.0;
        }

/* compute membership, and update centers for each pixel */ i = pix-1;

do {

/*      for(i=0; i<pix; i++) {
*/
            /* get squared distances to each cluster center */ for(sum=0.0,j=0; j<nc; j++) {
                mu[j] = d2[j] = 0.0;
                d = (double)x[i] - cc0[j][0];
```

```
                e = (double)y[i] - cc0[j][1];
                dd = (d * d) + (e * e);
                if(dd > 0.0) {
/*                  printf("%.2f ", dd);
                    d2[j] = pow(1.0/dd, mm);
*/
                    f = 1.0/dd;
                d2[j] = (f * f * f);
                    sum += d2[j];
                }
            }

/* compute membership %'s */ for(fl=j=0; j<nc; j++)
                if(d2[j] == 0.0) {fl=1; break;} if(fl) mu[j] = 1.0;
            else {
              for(j=0; j<nc; j++) {
                mu[j] = d2[j]/sum;
/*              printf("\nMembership is %f\n", mu[j]);
    */

}
            }

/* update numerator, denominator for cluster centers */ for(j=0; j<nc; j++) {
/*              m2 = pow(mu[j], m);

m2 = mu[j] * mu[j];
*/
                ii = mem[j][i] = (UCHAR)(100.0 * (mu[j] + 0.0005));

m2 = msq[ii];

den[j] += m2;
                num[j][0] += (m2 * (double)x[i]);
                num[j][1] += (m2 * (double)y[i]);

mn[j] += mu[j];

}

}
        while(i--);     /* end of sample loop */

/*      printf("\nout of sample loop\n");
    */
        /* compute new cluster center location, mean value */ for(j=0; j<nc; j++) {
/*          printf("\nnum = %f, den[%d] = %f\n", num[j][0], j, den[j]);
    */
            cc1[j][0] = num[j][0]/den[j];
            cc1[j][1] = num[j][1]/den[j];
            mn[j] /= xx;

/*      printf("\nAmount for compartment %d = %f\n", j, mn[j]);
    */

}

/* check difference in cluster centers from previous iteration */
```

```
        for(itflag = j = 0; j<nc; j++)
            if((fabs(cc1[j][0] - cc0[j][0]) + fabs(cc1[j][1] - cc0[j][1])) > eps)
                {itflag = 1; break;}

/*      printf("\nitflag = %d", itflag);
*/

}
    while(itflag);

printf("\n\nClustering complete ... ");

/*
    for(j=0; j<nc; j++)
        printf("\nOverall cluster center %d difference = %.2f  ",
            j+1, cc2[j] - cc1[j]);
*/
    printf("\n");

if(fluid != 0) {
        zz = (double)fluid;   /* fluid area measured by thresholding (kodalith) */
        yy = xx + zz;         /* total area used */ for(j=0; j<nc; j++) {
            ps = 100.0 * ((xx * mn[j])/yy);
            printf("\nPercentage of cluster %d = %5.1f, Center value = %3.0f ",
                j+1, ps, cc1[j][1]);
        }
        ps = 100.0 * (zz/yy);
        printf("\nPercentage of fluid cluster %d = %5.1f ", j+1, ps);
    }
    else {
        for(j=0; j<nc; j++) {
            ps = 100.0 * mn[j];
            printf("\nPercentage of cluster %d = %5.1f, Center value = %3.0f ",
                j+1, ps, cc1[j][1]);
        }
    }
    fluid = 0;

printf("\n\n");

/*
    if(nc == 2) cc1[2] = 0.0;
*/ zeroimage(0, &Result);

/* defuzzify and create result image */
    k = j = 0;

do { i = 0;

do {

/* use T2 image centroids as a basis */ if(getpixelgray(mask_image, i, j)) {
                pix1 = getpixelgray(src1_image, i, j);
                pix2 = getpixelgray(src2_image, i, j);
                if(pix1 && pix2) {
                    csf = (int)((cc1[0][1] * (double)mem[0][k])/100.0);
                    gry = (int)((cc1[1][1] * (double)mem[1][k])/100.0);
                    if(nc == 3)
                        wht = (int)((cc1[2][1] * (double)mem[2][k])/100.0);

val = csf + gry + wht;
                    setpixelgray(&Result, i, j, val);
                    k++;

fprintf(fp, "%d %d %d\n", pix1, pix2, val);

}
            }
```

```
            i++;

}
      while(i < 256);

j++;

}
   while(j < 256);

fclose(fp);
   pause();

}

/*
anterior_volume() {

/* computes white, gray, csf volumes anterior to line ((a,b), (c,d)) */

/* compute x(y) */ m = (double)(d - b)/(double)(c - a);

for(i=0; i<256; i++)
   csf = wht = gry = 0.0;

k = j = 0;

do { i = 0;

do {

/* use T2 image centroids as a basis */ if(getpixelgray(mask_image, i, j)) {
               pix1 = getpixelgray(src1_image, i, j);
               pix2 = getpixelgray(src2_image, i, j);
               if(pix1 && pix2) {
                  csf = (int)((cc1[0][1] * (double)mem[0][k])/100.0);
                  gry = (int)((cc1[1][1] * (double)mem[1][k])/100.0);
                  if(nc == 3)
                     wht = (int)((cc1[2][1] * (double)mem[2][k])/100.0);

val = csf + gry + wht;
                  setpixelgray(&Result, i, j, val);
                  k++;

fprintf(fp, "%d %d %d\n", pix1, pix2, val);

}
            }
         i++;

}
      while(i < 256);

j++;

}
   while(j < 256);

}
  */
```

```
UINT **calloc_2d_uint(int rows, int cols)
{

/* dynamically allocate and zero a 2d, long array on the near heap */ register int i, j;

UINT **m;

m = (UINT **)malloc((size_t)rows * sizeof(UINT *));
    if(!m) return(NULL);

for(i=0; i<rows; i++) {
        m[i] = (UINT *)malloc((size_t)cols * sizeof(UINT));
        if(!m[i]) return(NULL);
    } return(m);

}
```

What is claimed is:

1. A method of analyzing magnetic resonance images of a patient's brain to determine brain compartments, comprising:
providing pixelized magnetic resonance image data representative of a patient's brain; and
distinguishing at least two brain compartment types for said patient's brain utilizing a fuzzy clustering process and said pixelized magnetic resonance image data.

2. The method of claim 1, further comprising:
displaying a pixelized magnetic resonance solution image of said at least two distinguished brain compartment types.

3. The method of claim 1, further comprising:
determining brain compartment volumes for each of said at least two distinguished brain compartment types.

4. The method of claim 3, further comprising:
determining a percentage brain compartment volume for each of said at least two determined brain compartment volumes.

5. The method of claim 3, wherein said determining step comprises determining brain compartment volumes for cerebrospinal fluid, gray matter and white matter.

6. The method of claim 5, wherein said providing step comprises providing pixelized magnetic resonance image data obtained from a PD-weighted magnetic resonance image and a T2-weighted magnetic resonance image.

7. The method of claim 5, wherein said providing step comprises providing pixelized magnetic resonance image data obtained from a PD-weighted magnetic resonance image, a T2-weighted magnetic resonance image, and a T1-weighted magnetic resonance image.

8. The method of claim 5, wherein said fuzzy clustering process has a fuzzification factor (m) of about 1.2 to 1.4.

9. The method of claim 8, wherein said fuzzification factor (m) is an integer ratio of 4 over 3 (4/3).

10. The method of claim 5, wherein said fuzzy clustering process has a centroid difference error convergence approach.

11. The method of claim 10, wherein said fuzzy clustering process has a centroid difference error convergence approach, comprising:
selecting a current centroid of a cluster representing each of said at least two distinguished brain compartment types;
determining a distance from a plurality of pixel vectors to each current centroid;
determining a membership vector for each of said plurality of pixel vectors in each cluster;
determining a new centroid for each cluster;
determining a difference between each of said new centroid for each cluster and said current centroid for each cluster;
substituting said new centroid value for said current centroid value for each cluster if said difference is greater than a desired error convergence threshold; and
returning to said step of determining a distance after substituting said new centroid value for said current centroid value for each cluster if said difference is greater than a desired error convergence threshold.

12. The method of claim 11, wherein said desired error convergence threshold is greater than 0.0 but less than 0.5.

13. A method of analyzing magnetic resonance images of a patient's brain to determine the presence or absence of a predetermined brain compartment level, comprising:
providing pixelized magnetic resonance image data representative of a patient's brain;
determining a brain compartment level for at least one brain compartment type of said patient's brain utilizing a fuzzy clustering process and said pixelized magnetic resonance image data; and
comparing said brain compartment level for at least one of said at least one brain compartment type with a predetermined brain compartment level for said at least one of said at least one brain compartment type to determine the presence or absence of said predetermined brain compartment level.

14. The method of claim 13, wherein said determining step comprises determining a brain compartment level of cerebrospinal fluid, gray matter and white matter.

15. The method of claim 14, wherein said fuzzy clustering process has a fuzzification factor (m) of about 1.2 to 1.4.

16. The method of claim 15, wherein said fuzzification factor (m) is an integer ratio of 4 over 3 (4/3).

17. The method of claim 14, wherein said fuzzy clustering process has a centroid difference error convergence approach.

18. The method of claim 17, wherein said fuzzy clustering process has a centroid difference error convergence approach, comprising:
   selecting a current centroid of a cluster representing each of said at least two distinguished brain compartment type;
   determining a distance from a plurality of pixel vectors to each current centroid;
   determining a membership vector for each of said plurality of pixel vectors in each cluster;
   determining a new centroid for each cluster;
   determining a difference between each of said new centroid for each cluster and said current centroid for each cluster;
   substituting said new centroid value for said current centroid value for each cluster if said difference is greater than a desired error convergence threshold; and
   returning to said step of determining a distance after substituting said new centroid value for said current centroid value for each cluster if said difference is greater than a desired error convergence threshold.

19. The method of claim 17, wherein said desired error convergence threshold is greater than 0.0 but less than 0.5.

20. The method of claim 13, further comprising:
   indicating a brain condition based upon said presence or absence of said predetermined brain compartment level for said at least one of said at least one brain compartment type.

21. The method of claim 20, wherein said determining step comprises determining a percentage brain compartment volume for cerebrospinal fluid, gray matter and white matter; and said comparing step comprising, comparing said determined percentage brain compartment volume for said cerebrospinal fluid with a predetermined percentage brain compartment volume for said cerebrospinal fluid.

22. The method of claim 13, wherein said determining step comprises determining a brain compartment level for cerebrospinal fluid.

23. The method of claim 21, wherein said indicating step comprises indicating hydrocephalus.

24. The method of claim 23, wherein said predetermined percentage brain compartment volume for said cerebrospinal fluid is about ten percent.

25. An apparatus for a analyzing magnetic resonance images of a patient's brain to determine brain compartments, comprising:
   an input means for receiving pixelized magnetic resonance image data representative of a patient's brain;
   a memory means coupled to said input means for storing said pixelized magnetic resonance image data; and
   a microprocessor means coupled to said memory means and coupled to said input means for distinguishing at least two brain compartment types for said patient's brain utilizing a fuzzy clustering process and said pixelized magnetic resonance image data.

26. The apparatus of claim 25, further comprising:
   an output means coupled to said microprocessor means for displaying a pixelized magnetic resonance solution image.

27. The apparatus of claim 25, wherein said microprocessor means is also for determining brain compartment volumes for each of said at least two distinguished brain compartment types.

28. The apparatus of claim 27, wherein said at least two brain compartment types are cerebrospinal fluid gray matter and white matter.

29. The apparatus of claim 28, wherein said fuzzy clustering process has a fuzzification factor (m) of about 1.2 to 1.4.

30. The apparatus of claim 28, wherein said fuzzy clustering process has a centroid difference error convergence approach.

31. The apparatus of claim 30, wherein said fuzzy clustering process has an error convergence threshold greater than 0.0 but less than 0.5.

32. An apparatus for analyzing magnetic resonance images of a patient's brain to determine the presence or absence of a predetermined brain compartment level, comprising:
   an input means for receiving pixelized magnetic resonance image data representative of a patient's brain;
   a memory means coupled to said input means for storing said pixelized magnetic resonance image data; and
   a microprocessor means coupled to said memory means and coupled to said input means for determining a brain compartment level for at least one brain compartment type in said patient's brain utilizing a fuzzy clustering process and said pixelized magnetic resonance image data, and for comparing said brain compartment level for at least one of said at least one brain compartment type with a predetermined brain compartment level for at least one of said at least gone brain compartment type to determine the presence or absence of said predetermined brain compartment level.

33. The apparatus of claim 32, further comprising:
   an output means coupled to said microprocessor means for displaying an indication of said presence or absence of said predetermined brain compartment level for at least one of said at least one brain compartment type.

34. The apparatus of claim 32, wherein said at least two brain compartment types are cerebrospinal fluid, gray matter and white matter.

35. The apparatus of claim 34, wherein said fuzzy clustering process has a fuzzification factor (m) of about 1.2 to 1.4.

36. The apparatus of claim 34, wherein said fuzzy clustering process has a centroid difference error convergence approach.

37. The apparatus of claim 36, wherein said fuzzy clustering process has a convergence threshold greater than 0.0 but less than 0.5.

38. The apparatus of claim 34, wherein said microprocessor means is also for indicating a brain condition based upon said presence or absence of said predetermined brain compartment level for at least one of said at least one brain compartment type.

39. The apparatus of claim 38, wherein said brain compartment level is a percentage brain compartment volume; wherein said predetermined brain compartment level is a predetermined percentage brain compartment volume of cerebrospinal fluid; and wherein said brain condition is hydrocephalus.

* * * * *

UNITED STATES PATENT AND TRADEMARK OFFICE
CERTIFICATE OF CORRECTION

PATENT NO. : 5,425,368

DATED : June 20, 1995

INVENTOR(S) : Michael E. Brandt

It is certified that error appears in the above-identified patent and that said Letters Patent is hereby corrected as shown below:

In claim 32, column 88, line 34, delete "gone" and insert --one--.

Signed and Sealed this

Nineteenth Day of September, 1995

Attest:

BRUCE LEHMAN

Attesting Officer    Commissioner of Patents and Trademarks